US012247827B2

(12) United States Patent
Okuma et al.

(10) Patent No.: US 12,247,827 B2
(45) Date of Patent: Mar. 11, 2025

(54) BEAD APPEARANCE INSPECTION DEVICE, BEAD APPEARANCE INSPECTION METHOD, PROGRAM, AND BEAD APPEARANCE INSPECTION SYSTEM

(71) Applicant: Panasonic Intellectual Property Management Co., Ltd., Osaka (JP)

(72) Inventors: Katsuaki Okuma, Osaka (JP); Kazuyuki Nakashima, Osaka (JP); Teruaki Nishinaka, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 183 days.

(21) Appl. No.: 17/901,438

(22) Filed: Sep. 1, 2022

(65) Prior Publication Data

US 2022/0412728 A1 Dec. 29, 2022

Related U.S. Application Data

(63) Continuation of application No. PCT/JP2021/008242, filed on Mar. 3, 2021.

(30) Foreign Application Priority Data

Mar. 5, 2020 (JP) .................. 2020-038205

(51) Int. Cl.
*G01N 33/207* (2019.01)
*G01B 11/24* (2006.01)
*G01N 21/88* (2006.01)

(52) U.S. Cl.
CPC ............. *G01B 11/24* (2013.01); *G01N 21/88* (2013.01); *G01N 33/207* (2019.01)

(58) Field of Classification Search
CPC ....... G01B 11/24; G01N 33/207; G01N 21/88
See application file for complete search history.

(56) References Cited

U.S. PATENT DOCUMENTS 5,495,090 A 2/1996 Mukai et al.
9,733,219 B2 * 8/2017 Spencer ............. G01N 29/0645
(Continued)

FOREIGN PATENT DOCUMENTS

CN 107073627 8/2017
JP 2770570 7/1998
(Continued)

OTHER PUBLICATIONS

First Office Action issued Sep. 21, 2023 in corresponding Chinese Patent Application No. 2021800189083, with partial English language translation.

(Continued)

*Primary Examiner* — Jonathan M Hansen
*Assistant Examiner* — Jarreas Underwood
(74) *Attorney, Agent, or Firm* — Wenderoth, Lind & Ponack, L.L.P.

(57) ABSTRACT

A bead appearance inspection device includes an input unit configured to enter input data related to a welding bead of a workpiece produced by welding, and a determination unit configured to perform an inspection determination related to a shape of the welding bead based on the input data. The determination unit determines which of a range of a value indicating a non-defective product zone, a range of a value indicating a gray zone, and a range of a value indicating a defective product zone a value obtained from the input data belongs to. The range of the value indicating the gray zone is between the range of the value indicating the non-defective product zone and the range of the value indicating the defective product zone.

7 Claims, 17 Drawing Sheets

(56) References Cited

U.S. PATENT DOCUMENTS

| | | | |
|---|---|---|---|
| 2006/0249274 A1 | 11/2006 | Mutsaarts | |
| 2011/0183304 A1* | 7/2011 | Wallace | G09B 19/24 |
| | | | 434/234 |
| 2015/0001196 A1* | 1/2015 | Kim | B23K 31/125 |
| | | | 219/121.83 |
| 2015/0060424 A1* | 3/2015 | Daniel | B23K 31/12 |
| | | | 219/130.21 |
| 2016/0203732 A1* | 7/2016 | Wallace | G09B 7/00 |
| | | | 434/234 |
| 2016/0320344 A1* | 11/2016 | Spencer | G01N 29/265 |
| 2019/0321905 A1* | 10/2019 | Wang | B23K 9/167 |
| 2019/0377027 A1* | 12/2019 | Rivoir | G01R 31/31708 |

FOREIGN PATENT DOCUMENTS

| | | |
|---|---|---|
| JP | 2000-167666 | 6/2000 |
| JP | 2003-194669 | 7/2003 |
| JP | 2006-528070 | 12/2006 |
| JP | 2008-076322 | 4/2008 |
| JP | 2012-37487 | 2/2012 |
| JP | 2013-22597 | 2/2013 |
| JP | 2013022597 A * | 2/2013 |
| JP | 2017-148841 | 8/2017 |
| JP | 2020-024121 | 2/2020 |
| JP | 2021-048286 | 3/2021 |

OTHER PUBLICATIONS

International Search Report dated May 11, 2021 in International Application No. PCT/JP2021/008242.

\* cited by examiner

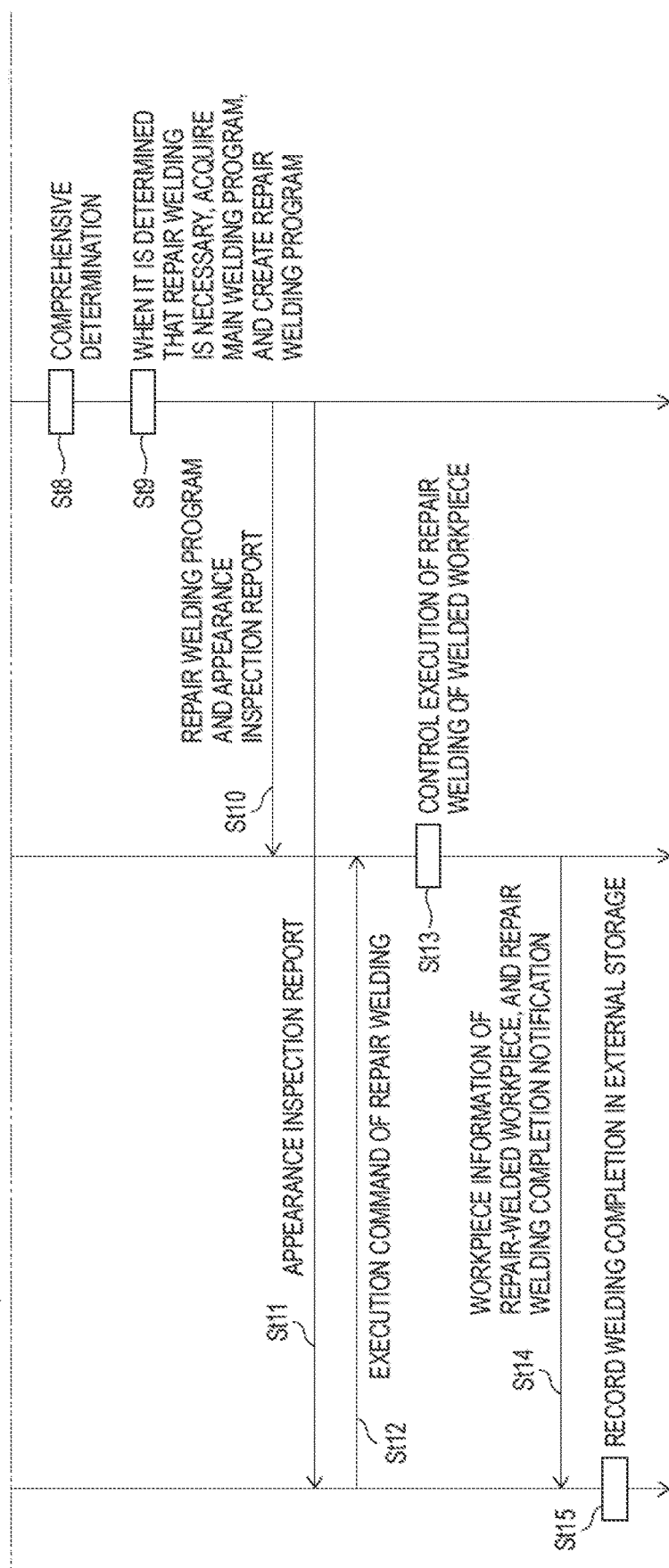

FIG. 5

| | SHAPE COMPARISON WITH MASTER DATA | MISSING OF BEAD | POSITIONAL DEVIATION OF BEAD | HOLE | PIT | UNDERCUT | SPUTTERING | PROTRUSION |
|---|---|---|---|---|---|---|---|---|
| FIRST APPEARANCE INSPECTION | ○ | ○ | ○ | △ | × | △ | × | × |
| SECOND APPEARANCE INSPECTION | SINCE THESE ITEMS CAN BE DETECTED BY FIRST APPEARANCE INSPECTION, THESE ITEMS ARE NOT DETECTION TARGETS IN SECOND APPEARANCE INSPECTION | | | ○ | ○ | ○ | ○ | ○ |
| FIRST APPEARANCE INSPECTION + SECOND APPEARANCE INSPECTION | ○ | ○ | ○ | ○ | ○ | ○ | ○ | ○ |

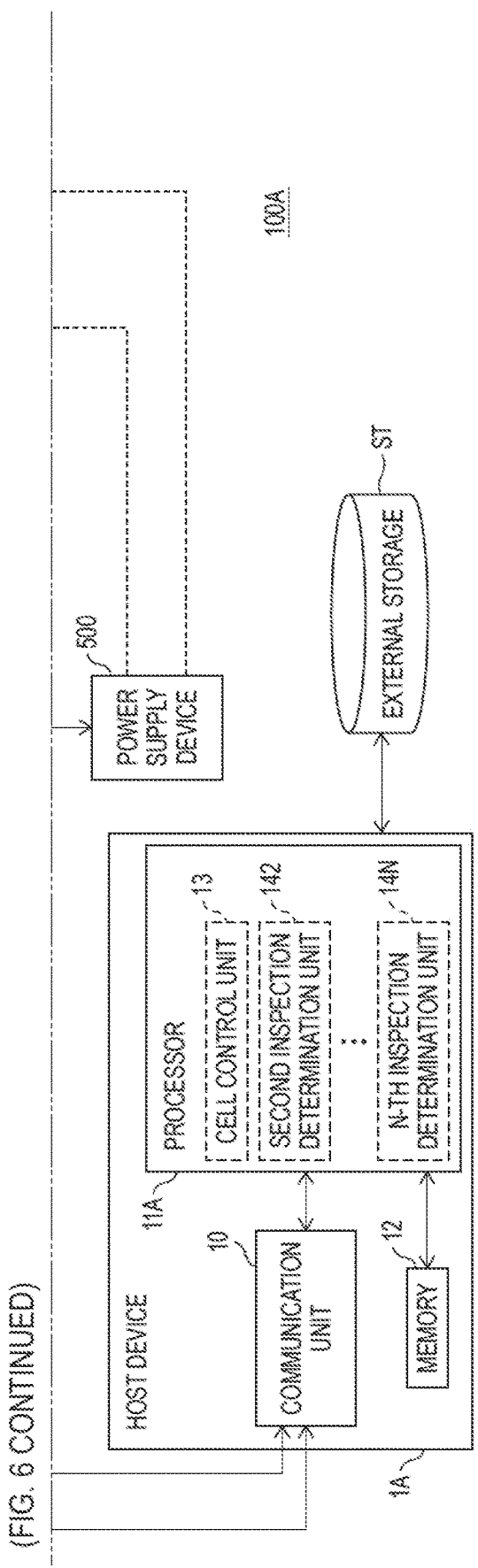

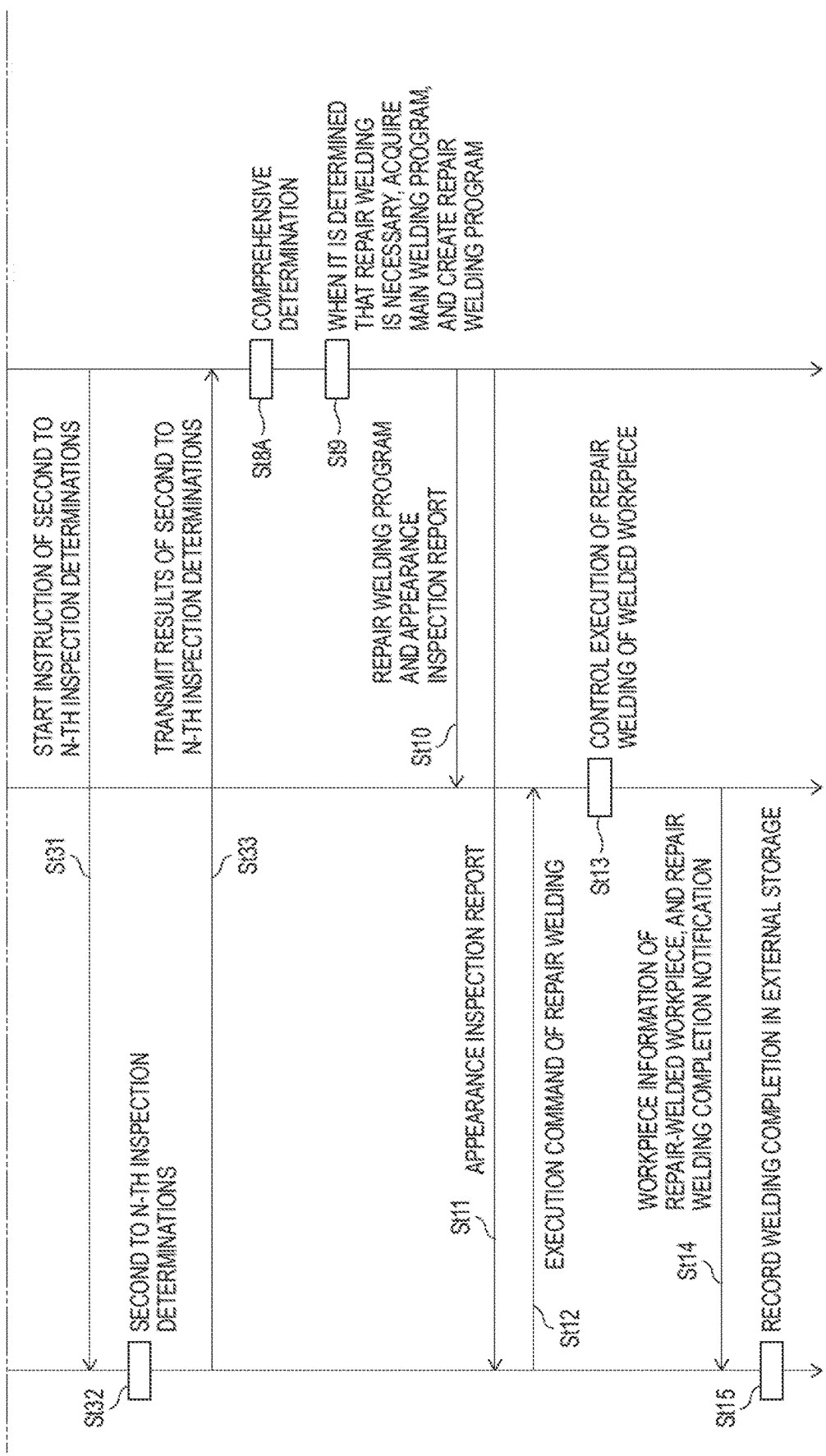

BEAD APPEARANCE INSPECTION DEVICE, BEAD APPEARANCE INSPECTION METHOD, PROGRAM, AND BEAD APPEARANCE INSPECTION SYSTEM

CROSS-REFERENCE TO RELATED APPLICATIONS

This is a continuation of International Application No. PCT/JP2021/008242 filed on Mar. 3, 2021, and claims priority from Japanese Patent Application No. 2020-038205 filed on Mar. 5, 2020, the entire content of which is incorporated herein by reference.

TECHNICAL FIELD

The present disclosure relates to a bead appearance inspection device, a bead appearance inspection method, a program, and a bead appearance inspection system.

BACKGROUND ART

PTL 1 discloses a shape inspection device that projects slit light onto a welding bead, images shape lines sequentially formed on the welding bead by scanning with the slit light, and acquires a three-dimensional shape of the welding bead as point group data based on imaging data of the sequentially formed shape lines. The shape inspection device sets an optional cutting line different from the shape line formed by scanning the welding bead displayed based on the point group data with the slit light in accordance with an input, and calculates a cross-sectional shape of the welding bead at the cutting line based on the point group data corresponding to the cutting line. Further, the shape inspection device compares various pieces of feature data calculated in accordance with the calculated cross-sectional shape with allowable ranges of the various pieces of feature data registered in advance, and determines whether the feature data is defective or non-defective.

CITATION LIST

Patent Literature

[PTL 1]: JP-A-2012-37487

SUMMARY OF INVENTION

Technical Problem

The present disclosure provides a bead appearance inspection device, a bead appearance inspection method, a program, and a bead appearance inspection system that more efficiently perform a bead appearance inspection of a workpiece produced by main welding.

Solution to Problem

The present disclosure provides a bead appearance inspection device including: an input unit configured to enter input data related to a welding bead of a workpiece produced by welding; and a determination unit configured to perform an inspection determination related to a shape of the welding bead based on the input data, in which the determination unit determines which of a range of a value indicating a non-defective product zone, a range of a value indicating a gray zone, and a range of a value indicating a defective product zone a value obtained from the input data belongs to, and in which the range of the value indicating the gray zone is between the range of the value indicating the non-defective product zone and the range of the value indicating the defective product zone.

Further, the present disclosure provides a bead appearance inspection method executed by a bead appearance inspection device, the bead appearance inspection method including: a step of inputting input data related to a welding bead of a workpiece produced by welding; and a determination step of performing an inspection determination related to a shape of the welding bead based on the input data, in which in the determination step, it is determined which of a range of a value indicating a non-defective product zone, a range of a value indicating a gray zone, and a range of a value indicating a defective product zone a value obtained from the input data belongs to, and in which the range of the value indicating the gray zone is between the range of the value indicating the non-defective product zone and the range of the value indicating the defective product zone.

Further, the present disclosure provides a program for causing a bead appearance inspection device, which is a computer, to execute: a step of inputting input data related to a welding bead of a workpiece produced by welding; and a determination step of performing an inspection determination related to a shape of the welding bead based on the input data, in which in the determination step, it is determined which of a range of a value indicating a non-defective product zone, a range of a value indicating a gray zone, and a range of a value indicating a defective product zone a value obtained from the input data belongs to, and in which the range of the value indicating the gray zone is between the range of the value indicating the non-defective product zone and the range of the value indicating the defective product zone.

Further, the present disclosure provides a bead appearance inspection system including: an input unit configured to enter input data related to a welding bead of a workpiece produced by welding; and a determination unit configured to perform an inspection determination related to a shape of the welding bead based on the input data, in which the determination unit determines which of a range of a value indicating a non-defective product zone, a range of a value indicating a gray zone, and a range of a value indicating a defective product zone a value obtained from the input data belongs to, and the range of the value indicating the gray zone is between the range of the value indicating the non-defective product zone and the range of the value indicating the defective product zone.

Advantageous Effects of Invention

According to the present disclosure, a bead appearance inspection of a workpiece produced by main welding can be more efficiently performed.

BRIEF DESCRIPTION OF DRAWINGS

FIG. 12 is a conceptual diagram showing a display example of a bead appearance inspection result by monitors MN1 and MN2, and the like.

DESCRIPTION OF EMBODIMENTS

Background of Present Disclosure

Figure 1:
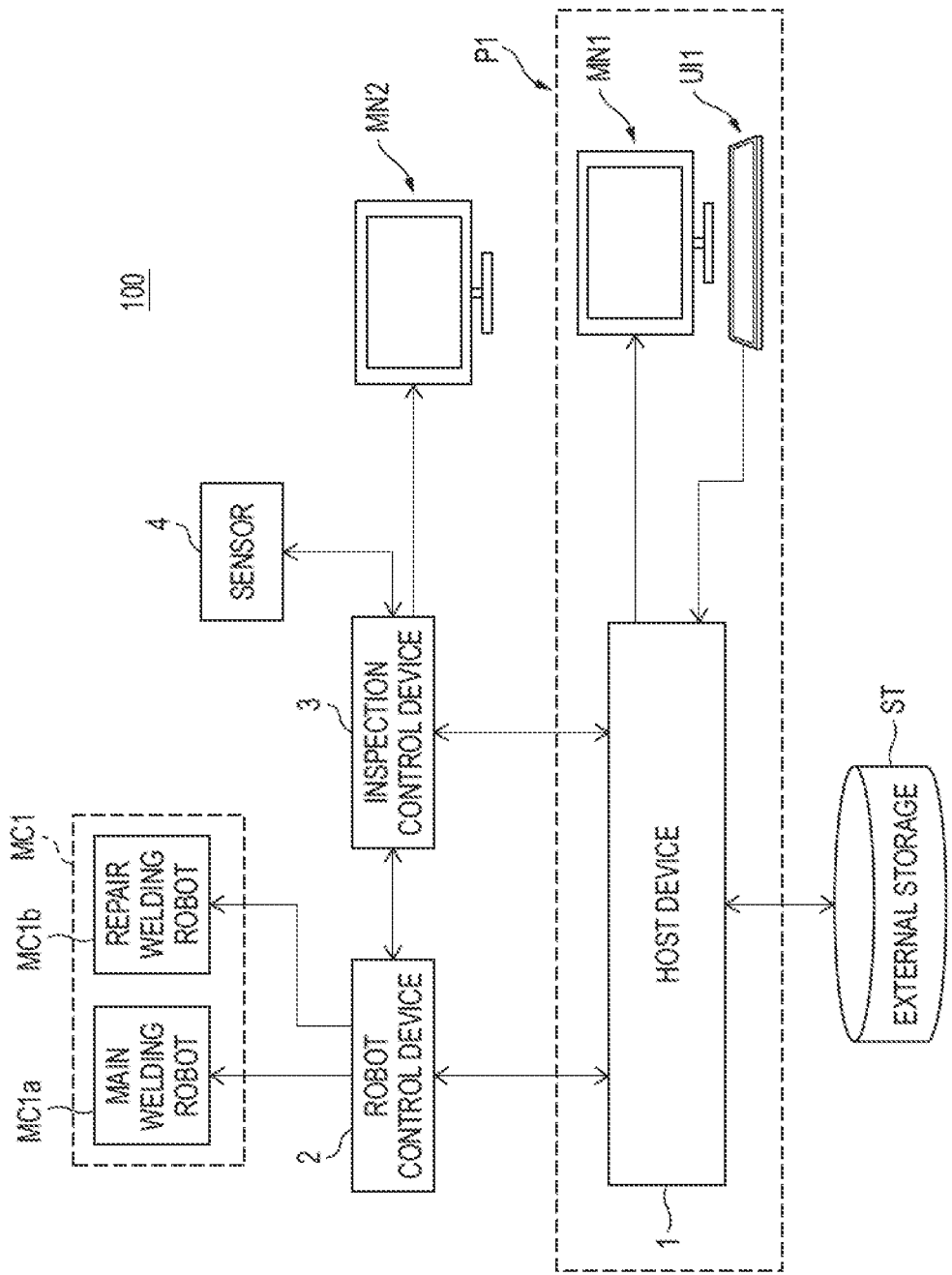
FIG. 1 is a schematic diagram showing a system configuration example of a welding system.

As disclosed in PTL 1, a device configuration for automatically performing an appearance shape inspection of a welding bead, such as determining a non-defective product when a calculated value of feature data (for example, a bead width, a bead height, or the like) related to a shape of a welding bead of a workpiece produced by main welding is within an allowable range, has been known in the related art. However, at an actual welding site, an operator often visually inspects quality of an appearance of the welding bead to determine whether the main welding of the workpiece is successful.

In the appearance inspection of the welding bead, in addition to the feature data related to the shape of the welding bead described above, there may be a wide variety of inspection items such as a positional deviation of the welding bead, presence or absence of a hole, and presence or absence of a welding defect such as sputtering. Further, depending on a user, a standard for determining whether a product is determined to be a non-defective product is often not uniform. Therefore, in the appearance inspection of the welding bead, it is considered that there is room for improvement for the related art in that, in consideration of not only the fact that the inspection item is different for each user but also the fact that quality of a workpiece that is a finished product is different for each user, customizability capable of optionally adjusting the inspection item and usability of the appearance inspection are further required.

Therefore, in the following embodiments, examples of a bead appearance inspection device, a bead appearance inspection method, a program, and a bead appearance inspection system that more efficiently perform bead appearance inspection of a workpiece produced by main welding will be described.

Further, in the appearance inspection of the welding bead, a threshold is set for a measured value such as a size of a defective portion of welding, or the number of defective portions of the welding, and the measured value is compared with the threshold, so that whether the welding is defective or non-defective may be determined. However, since a quality standard may be different for each user and it is also necessary to comprehensively consider characteristics of the workpiece and the like, it is not easy to determine an optimum threshold for determination. Therefore, determination accuracy of the appearance inspection of a workpiece in a boundary region between a non-defective product and a defective product may decrease, and situations such as overlooking a defective product and erroneously detecting a non-defective product as a defective product may occur. These situations reduce productivity of a product on which welding is performed.

Therefore, in the following embodiments, examples of a bead appearance inspection device, a bead appearance inspection method, a program, and a bead appearance inspection system will be described which improve productivity of a product on which welding is performed, by providing a determination classification of a gray zone in a boundary region between a non-defective product and a defective product, and when a gray determination is performed, performing a visual check by a user, a re-appearance inspection under more precise conditions, and the like.

Hereinafter, embodiments specifically disclosing the bead appearance inspection device, the bead appearance inspection method, the program, and the bead appearance inspection system according to the present disclosure will be described in detail with reference to the drawings as appropriate. However, unnecessarily detailed description may be omitted. For example, detailed description of a well-known matter or repeated description of a substantially the same configuration may be omitted. This is to avoid unnecessary redundancy of the following description and to facilitate understanding of those skilled in the art. It should be noted that the accompanying drawings and the following description are provided to enable those skilled in the art to fully understand the present disclosure, and are not intended to limit the range of the claims.

First Embodiment

A bead appearance inspection device according to a first embodiment inputs input data related to a welding bead of a workpiece produced by main welding, uses the input data and master data of a non-defective workpiece, and performs a first inspection determination related to a shape of the welding bead based on a comparison between the input data and the master data, and is equipped with k (k: an integer of 1 or more) types of artificial intelligence, and performs a second inspection determination related to a welding defect of the welding bead based on processings of the k types of artificial intelligence targeting the input data. The welding defect of the welding bead includes, for example, a hole, a pit, an undercut, sputtering, and a protrusion. The welding defect is not limited to those described above. The bead appearance inspection device outputs a result of an appearance inspection of the welding bead to an output device based on determination results of a first appearance inspection and the k second inspection determinations.

Hereinafter, a target object (for example, a metal) to be main-welded is defined as an "original workpiece", a target object produced (manufactured) by the main welding is defined as a "workpiece", and a target object whose defective portion of welding detected in an appearance inspection of the "workpiece" is repair-welded is defined as a "repair workpiece".

A step of producing a workpiece by joining an original workpiece to another original workpiece by a welding robot is defined as the "main welding", and a step of correcting such as repairing a defective portion of the workpiece by the welding robot is defined as the "repair welding".

The "workpiece" or the "repair workpiece" is not limited to a workpiece produced by one main welding, and may be a composite workpiece produced by two or more main welding.

(Configuration of Welding System)

FIG. 1 is a schematic diagram showing a system configuration example of a welding system 100. The welding system 100 includes a host device 1 connected to each of an external storage ST, an input interface UI1, and a monitor MN1, a robot control device 2, an inspection control device 3, a sensor 4, a main welding robot MC1$a$, and a repair welding robot MC1$b$. The main welding robot MC1$a$ and the repair welding robot MC1$b$ may be configured as separate robots, or may be configured as the single welding robot MC1. In order to facilitate understanding of the following description, it is assumed that both a main welding step and a repair welding step are executed by the welding robot MC1. Although only one pair of one robot control device 2, the main welding robot MC1$a$, and the repair welding robot MC1$b$ are shown in FIG. 1, a plurality of pairs may be provided. In FIG. 1, the sensor 4 is shown as a separate body from the welding robot MC1, but may be provided integrally with the welding robot MC1 (see FIG. 2).

The host device 1 integrally controls start and completion of the main welding executed by the welding robot MC1 via the robot control device 2. For example, the host device 1 reads out welding-related information input or set in advance by the user (for example, a welding operator or a system administrator, the same applies hereinafter) from the external storage ST, generates an execution command of main welding including content of the welding-related information by using the welding-related information, and transmits the execution command to the corresponding robot control device 2. When the main welding by the welding robot MC1 is completed, the host device 1 receives a main welding completion report indicating that the main welding by the welding robot MC1 is completed from the robot control device 2, updates a status to a status indicating that the corresponding main welding is completed, and records the status in the external storage ST. The execution command of the main welding described above is not limited to being generated by the host device 1, and may be generated by, for example, an operation panel (for example, a programmable logic controller (PLC)) of equipment in a factory or the like where the main welding is performed, or an operation panel (for example, a teach pendant (TP)) of the robot control device 2. The teach pendant (TP) is a device for operating the welding robot MC1 connected to the robot control device 2.

The host device 1 integrally controls the start and completion of the bead appearance inspection using the robot control device 2, the inspection control device 3, and the sensor 4. For example, when receiving the main welding completion report from the robot control device 2, the host device 1 generates an execution command of the bead appearance inspection of the workpiece produced by the welding robot MC1, and transmits the generated execution command to the robot control device 2 and the inspection control device 3. When the bead appearance inspection is completed, the host device 1 receives an appearance inspection report indicating that the bead appearance inspection is completed from the inspection control device 3, updates a status to a status indicating that the corresponding bead appearance inspection is completed, and records the status in the external storage ST.

The host device 1 integrally controls the start and completion of repair welding executed by the welding robot MC1 via the robot control device 2. For example, when receiving the appearance inspection report from the inspection control device 3, the host device 1 generates an execution command of the repair welding of the workpiece produced by the welding robot MC1 and transmits the generated execution command to the robot control device 2. When the repair welding is completed, the host device 1 receives a repair welding completion report indicating that the repair welding is completed from the robot control device 2, updates a status to a status indicating that the corresponding repair welding is completed, and records the status in the external storage ST.

Here, the welding-related information is information indicating content of the main welding executed by the welding robot MC1. The welding-related information is created in advance for each step of the main welding and is registered in the external storage ST. The welding-related information includes, for example, the number of original workpieces used in the main welding, workpiece information including an ID, a name, and a welding portion of the original workpiece used in the main welding, a scheduled execution date on which the main welding is executed, the number of workpieces to be welded and produced, and various welding conditions at the time of the main welding. The welding-related information may not be limited to data of items described above. The robot control device 2 causes the welding robot MC1 to start execution of the main welding using the original workpiece designated by the execution command based on the execution command of the main welding transmitted from the host device 1. The welding-related information described above is not limited to being managed by the host device 1 with reference to the external storage ST, and may be managed by, for example, the robot control device 2. In this case, since the robot control device 2 can grasp a state where the main welding is completed, an actual execution date may be managed instead of the scheduled execution date on which a welding step is executed in the welding-related information. In the present specification, although the type of the main welding is not limited, a step of producing one workpiece by joining a plurality of original workpieces will be described as an example in order to facilitate understanding of the description.

The host device 1 is connected to the monitor MN1, the input interface UI1, and the external storage ST so as to be able to input and output data, and is further connected to the robot control device 2 so as to be able to communicate data. The host device 1 may be a terminal device P1 integrally including the monitor MN and the input interface UI1, and may further integrally include the external storage ST. In this case, the terminal device P1 is a personal computer (PC) used by the user prior to the execution of the main welding. The terminal device P1 is not limited to the PC described above, and may be a computer device having a communication function, such as a smartphone or a tablet terminal.

The monitor MN1 may be configured using a display device such as a liquid crystal display (LCD) or an organic EL (electroluminescence). The monitor MN1 may display, for example, a screen showing a notification indicating that the main welding is completed, a notification indicating that the bead appearance inspection is completed, or a notification indicating that the repair welding is completed, which is output from the host device 1. Further, instead of the monitor MN1 or together with the monitor MN1, a speaker (not shown) may be connected to the host device 1, and the host device 1 may output, via the speaker, the notification indicating that the main welding is completed, the notification indicating that the bead appearance inspection is completed, or a sound having content indicating that the repair welding is completed.

The input interface UI1 is a user interface that detects an input operation of the user and outputs the input operation to the host device 1, and may be configured using, for example, a mouse, a keyboard, or a touch panel. The input interface UI1 receives, for example, an input operation when the user creates the welding-related information or receives an input operation when the execution command of the main welding is transmitted to the robot control device 2.

The external storage ST is configured using, for example, a hard disk drive or a solid state drive. The external storage ST stores, for example, data of the welding-related information created for each main welding, a status (production status) of a workpiece produced by the main welding or a repair workpiece repaired or the like by the repair welding, and workpiece information (see the above description) of the workpiece or the repair workpiece.

The robot control device 2, which is an example of the bead appearance inspection device, is connected to the host device 1 so as to be able to communicate data with the host device 1, and is connected to the welding robot MC1 so as to be able to communicate data with the welding robot MC1. When receiving the execution command of the main welding transmitted from the host device 1, the robot control device 2 controls the corresponding welding robot MC1 and causes the welding robot MC1 to execute the main welding based on the execution command. When detecting that the main welding is completed, the robot control device 2 generates a main welding completion report indicating that the main welding is completed, and notifies the host device 1 of the main welding completion report. Accordingly, the host device 1 can appropriately detect the completion of the main welding by the robot control device 2. A method for detecting the completion of the main welding by the robot control device 2 may be, for example, a method for determining the completion of the main welding based on a signal indicating the completion of the main welding from a sensor (not shown) provided in a wire feeding device 300, or may be a known method, and content of the method for detecting the completion of the main welding may not be limited.

When receiving the execution command of the bead appearance inspection transmitted from the host device 1, the robot control device 2 controls the welding robot MC1 (see FIG. 2) to which the sensor 4 is attached to execute the bead appearance inspection of the corresponding workpiece based on the execution command in accordance with an appearance inspection program created or prepared in advance by the robot control device 2. The appearance inspection report indicating that the bead appearance inspection is completed is transmitted from the inspection control device 3 to the host device 1, but may be transmitted from the robot control device 2 itself or from the robot control device 2 that has received an instruction from the inspection control device 3 to the host device 1. Accordingly, the host device 1 can appropriately detect the completion of the bead appearance inspection.

When receiving the execution command of the repair welding transmitted from the host device 1, the robot control device 2 controls the corresponding welding robot MC1 to cause the corresponding welding robot MC1 to execute the repair welding based on the execution command in accordance with a repair welding program created by the inspection control device 3. When detecting that the repair welding is completed, the robot control device 2 generates a repair welding completion report indicating that the repair welding is completed, and notifies the host device 1 of the repair welding completion report. Accordingly, the host device 1 can appropriately detect the completion of the repair welding based on the robot control device 2. A method for detecting the completion of the repair welding by the robot control device 2 may be, for example, a method for determining the completion of the repair welding based on a signal indicating the completion of the repair welding from a sensor (not shown) provided in a wire feeding device 300, or may be a known method, and content of the method for detecting the completion of the repair welding may not be limited.

The welding robot MC1 is connected to the robot control device 2 so as to be able to communicate data with the robot control device 2. The welding robot MC1 executes the main welding or the repair welding commanded from the host device 1 under control of the corresponding robot control device 2. As described above, the welding robot MC1 may include the main welding robot MC1a provided for the main welding and the repair welding robot MC1b provided for the repair welding. Further, when the sensor 4 is integrally attached to the welding robot MC1, the welding robot MC1 supports the execution of the bead appearance inspection commanded from the host device 1 by moving the sensor 4 along a movement trajectory of the welding robot MC1 during the main welding or during the repair welding in accordance with the appearance inspection program.

The inspection control device 3, which is an example of the bead appearance inspection device, is connected to the host device 1, the robot control device 2, and the sensor 4 so as to be able to communicate data with each other. When receiving the execution command of the bead appearance inspection transmitted from the host device 1, the inspection control device 3 executes the bead appearance inspection of a welding portion of the workpiece produced by the welding robot MC1 (for example, an inspection as to whether a welding bead formed on the workpiece satisfies a predetermined welding standard) together with the sensor 4. Although details of the bead appearance inspection will be described later with reference to FIGS. 4 and 5, for example, the inspection control device 3 performs the bead appearance inspection based on a comparison with master data of a non-defective workpiece predetermined for each workpiece by using input data (for example, point group data capable of specifying a three-dimensional shape of a welding bead) related to a shape of a welding bead acquired by the sensor 4 based on welding portion information of the workpiece included in the execution command of the bead appearance inspection. Hereinafter, such a bead appearance inspection is defined as a "first inspection determination". Further, the inspection control device 3 is equipped with k (k: an integer of 1 or more) types of artificial intelligence (AI), and performs a bead appearance inspection in which neural networks based on the artificial intelligence are formed and presence or absence of a welding defect is determined based on the AI targeting the input data described above. Hereinafter, such a bead appearance inspection is defined as a "second inspection determination". In the first embodiment, the inspection control device 3 can execute the first inspection determination and the second inspection determination described above. The inspection control device 3 performs a comprehensive determination of the bead appearance inspections by using results obtained by executing the first inspection determination and the second inspection determination, generates an appearance inspection report including the comprehensive determination result and the notification indicating that the bead appearance inspection is completed, transmits the generated appearance inspection report to the host device 1, and outputs the generated appearance inspection report to a monitor MN2.

When determining that a welding defect is detected by the second inspection determination in the bead appearance inspection of the workpiece, the inspection control device 3 creates a repair welding program indicating that a correction such as repair of a portion of the welding defect is performed, by using an appearance inspection result including position information of the portion of the welding defect (a so-called detection point). The inspection control device 3 transmits the repair welding program and the appearance inspection result to the robot control device 2 in association with each other.

The sensor 4 is connected to the inspection control device 3 so as to be able to communicate data with the inspection control device 3. When the sensor 4 is attached to the welding robot MC1 (see FIG. 2), the sensor 4 can operate such that a placing table on which a workpiece Wk is placed can be three-dimensionally scanned in response to driving of a manipulator 200 based on control of the robot control device 2. The sensor 4 acquires data (for example, point group data OD1 described later) capable of specifying a three-dimensional shape of the workpiece placed on the placing table (see FIG. 2) to transmit the acquired data to the inspection control device 3 in response to driving of the manipulator 200 based on control of the robot control device 2.

The monitor MN2, which is an example of an output device, may be configured using a display device such as an LCD or an organic EL. The monitor MN2 displays, for example, a notification indicating that the bead appearance inspection is completed and output from the inspection control device 3, or a screen showing the notification and a result of the bead appearance inspection (for example, a result of the comprehensive determination described above). Further, instead of the monitor MN2 or together with the monitor MN2, a speaker (not shown) may be connected to the inspection control device 3, and the inspection control device 3 may output, via the speaker, the notification indicating that the bead appearance inspection is completed, or a sound indicating content of the notification and the result of the bead appearance inspection (for example, the result of the comprehensive determination described above).

Figure 2:
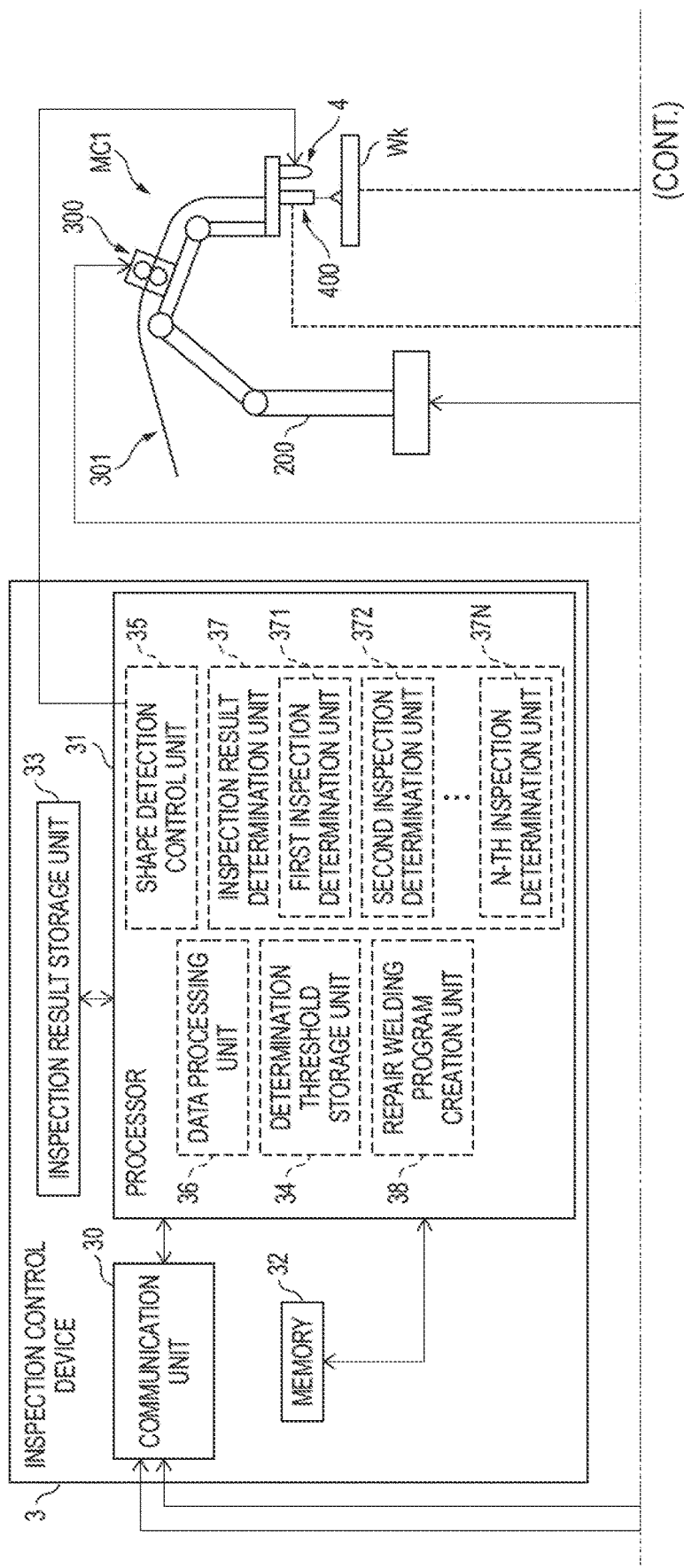
FIG. 2 is a diagram showing an internal configuration example of an inspection control device, a robot control device, and a host device according to a first embodiment.
Figure 2:
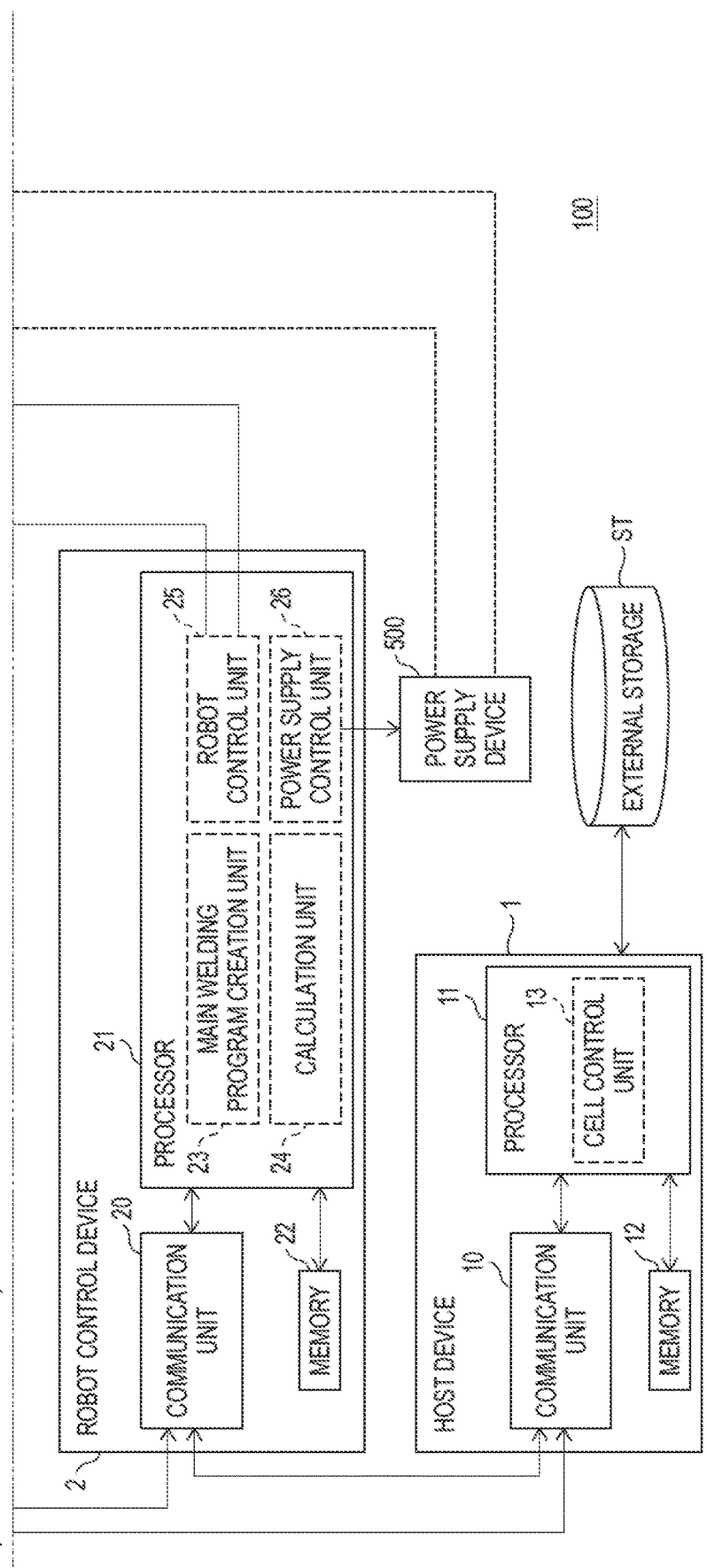

FIG. 2 is a diagram showing an internal configuration example of the inspection control device 3, the robot control device 2, and the host device 1 according to the first embodiment. In order to facilitate understanding of the description, showing the monitors MN1 and MN2 and the input interface UI1 is omitted in FIG. 2. The workpiece Wk shown in FIG. 2 may be an original workpiece placed before the main welding is performed, a workpiece that is a target of the bead appearance inspection (that is, a workpiece produced by the main welding), or a workpiece that is a target of the repair welding.

The welding robot MC1 executes various steps such as the main welding, movement of the sensor 4 during the bead appearance inspection, and the repair welding commanded from the host device 1 under control of the robot control device 2. The welding robot MC1 performs, for example, arc welding in the step of the main welding or the repair welding. However, the welding robot MC1 may perform welding (for example, laser welding or gas welding) other than the arc welding. In this case, although showing is omitted, a laser head, instead of a welding torch 400, may be connected to a laser oscillator via an optical fiber. The welding robot MC1 includes at least the manipulator 200, the wire feeding device 300, a welding wire 301, and the welding torch 400.

The manipulator 200 includes an articulated arm, and moves each arm based on a control signal from a robot control unit 25 of the robot control device 2. Accordingly, the manipulator 200 can change a positional relationship between the workpiece Wk and the welding torch 400 (for example, an angle of the welding torch 400 with respect to the workpiece Wk) by driving the arm.

The wire feeding device 300 controls a feeding speed of the welding wire 301 based on a control signal from the robot control device 2. The wire feeding device 300 may include a sensor (not shown) that can detect a remaining amount of the welding wire 301. Based on an output of the sensor, the robot control device 2 can detect that the step of the main welding or the repair welding is completed.

The welding wire 301 is held in the welding torch 400. When power is supplied from a power supply device 500 to the welding torch 400, an arc is generated between a tip end of the welding wire 301 and the workpiece Wk, and the arc welding is performed. For convenience of description, showing and description of the configuration and the like for supplying shielding gas to the welding torch 400 are omitted.

The host device 1 generates an execution command of various steps of the main welding, the bead appearance inspection, and the repair welding by using the welding-related information input or set in advance by the user, and transmits the generated execution command to the robot control device 2. As described above, when the sensor 4 is integrally attached to the welding robot MC1, the execution command of the bead appearance inspection is transmitted to both the robot control device 2 and the inspection control device 3. The host device 1 includes at least a communication unit 10, a processor 11, and a memory 12.

The communication unit 10 is connected to the robot control device 2 and the external storage ST so as to be able to communicate data with the robot control device 2 and the external storage ST. The communication unit 10 transmits, to the robot control device 2, the execution command of the various steps of the main welding, the bead appearance inspection, or the repair welding generated by the processor 11. The communication unit 10 receives the main welding completion report, the appearance inspection report, and the repair welding completion report transmitted from the robot control device 2, and outputs the received reports to the processor 11. The execution command of the main welding or the repair welding may include, for example, a control signal for controlling the manipulator 200, the wire feeding device 300, and the power supply device 500 provided in the welding robot MC1.

The processor 11 is configured using, for example, a central processing unit (CPU) or a field programmable gate array (FPGA), and performs various processings and controls in cooperation with the memory 12. Specifically, the processor 11 implements functions of a cell control unit 13 by referring to a program held in the memory 12 and executing the program.

The memory 12 includes, for example, a random access memory (RAM) serving as a work memory used when executing a processing of the processor 11, and a read only memory (ROM) for storing a program that defines the processing of the processor 11. The RAM temporarily stores data generated or acquired by the processor 11. A program that defines the processing of the processor 11 is written into the ROM. Further, the memory 12 stores data of the welding-related information read from the external storage ST, a status of the workpiece or the repair workpiece, and data of workpiece information (see the above description) of the workpiece or the repair workpiece transmitted from the robot control device 2.

The cell control unit 13 generates the execution command for executing the main welding, the bead appearance inspection of the workpiece, or the repair welding based on the welding-related information stored in the external storage ST. Further, the cell control unit 13 creates the appearance inspection program related to driving of the welding robot MC1 during the bead appearance inspection of the workpiece Wk (for example, the workpiece) after the main welding, and an execution command of the appearance inspection program including the appearance inspection program, based on the welding-related information stored in the external storage ST. The appearance inspection program may be created in advance and stored in the external storage ST. In this case, the cell control unit 13 simply reads and acquires the appearance inspection program from the external storage ST. The cell control unit 13 may generate different execution commands for various steps of the main welding or the repair welding executed by the welding robot MC1. The execution command of the main welding or the repair welding generated by the cell control unit 13 or the execution command of the appearance inspection program including the appearance inspection program is transmitted to the corresponding robot control device 2 or each of the robot control device 2 and the inspection control device 3 via the communication unit 10.

The robot control device 2 controls a processing of the corresponding welding robot MC1 (for example, the sensor 4, the manipulator 200, the wire feeding device 300, and the power supply device 500) based on the execution command of the main welding, the bead appearance inspection, or the repair welding transmitted from the host device 1. The robot control device 2 includes at least a communication unit 20, a processor 21, and a memory 22.

The communication unit 20 is connected to the host device 1, the inspection control device 3, and the welding robot MC1 so as to be able to communicate data with the host device 1, the inspection control device 3, and the welding robot MC1. Although showing is simplified in FIG. 2, data is transmitted and received between the robot control unit 25 and the manipulator 200, between the robot control unit 25 and the wire feeding device 300, and between a power supply control unit 26 and the power supply device 500 via the communication unit 20. The communication unit 20 receives the execution command of the main welding, the bead appearance inspection, or the repair welding transmitted from the host device 1. The communication unit 20 transmits the workpiece information of the workpiece produced by the main welding or the repair workpiece produced by the correction by the repair welding to the host device 1.

Here, the workpiece information includes not only an ID of the workpiece or the repair workpiece but also at least an ID, a name, a welding portion, a welding condition at the time of executing the main welding, and a welding condition at the time of executing the repair welding of an original workpiece used in the main welding. Further, the workpiece information may include information (for example, coordinates) indicating a position of a detection point indicating a defective portion of the workpiece. Further, the welding condition or the repair welding condition includes, for example, a material and a thickness of the original workpiece, a material and a wire diameter of the welding wire 301, a type of the shielding gas, a flow rate of the shielding gas, a set average value of a welding current, a set average value of a welding voltage, a feeding speed and a feeding amount of the welding wire 301, the number of times of welding, and a welding time. Further, the welding condition or the repair welding condition may also include, for example, information indicating a type of the main welding or the repair welding (for example, TIG welding, MAG welding, or pulse welding), and a moving speed and a moving time of the manipulator 200, in addition to the items described above.

The processor 21 is configured using, for example, a CPU or an FPGA, and performs various processings and controls in cooperation with the memory 22. Specifically, the processor 21 implements functions of a main welding program creation unit 23, a calculation unit 24, the robot control unit 25, and the power supply control unit 26 by referring to a program held in the memory 22 and executing the program.

The memory 22 includes, for example, a RAM serving as a work memory used when executing a processing of the processor 21, and a ROM for storing a program that defines the processing of the processor 21. The RAM temporarily stores data generated or acquired by the processor 21. A program that defines the processing of the processor 21 is written into the ROM. Further, the memory 22 stores data of the execution command of the main welding, the bead appearance inspection, or the repair welding transmitted from the host device 1, and data of the workpiece information of the workpiece produced by the main welding or the repair workpiece produced by the repair welding. Further, the memory 22 stores a main welding program of the main welding executed by the welding robot MC1. The main welding program is a program that defines a specific procedure (step) of the main welding in which a plurality of original workpieces are joined or the like using a welding condition in the main welding.

Based on the execution command of the main welding transmitted from the host device 1 via the communication unit 20, the main welding program creation unit 23 uses workpiece information (for example, an ID, a name, and a welding portion of the original workpiece) of each of the plurality of original workpieces included in an execution command to generate a main welding program of the main welding executed by the welding robot MC1. The main welding program may include various parameters such as a welding current, a welding voltage, an offset amount, a welding speed, and a posture of the welding torch 400 for controlling the power supply device 500, the manipulator 200, the wire feeding device 300, the welding torch 400, and the like during execution of the main welding. The main welding program may be stored in the processor 21, or may be stored in the RAM in the memory 22.

The calculation unit 24 performs various calculations. For example, based on the main welding program generated by the main welding program creation unit 23, the calculation unit 24 calculates parameters for controlling the welding robot MC1 (specifically, the manipulator 200, the wire feeding device 300, and the power supply device 500) controlled by the robot control unit 25.

Based on the main welding program generated by the main welding program creation unit 23, the robot control unit 25 generates a control signal for driving the welding robot MC1 (specifically, the manipulator 200, the wire feeding device 300, and the power supply device 500). The robot control unit 25 transmits the generated control signal to the welding robot MC1. Further, based on the appearance inspection program transmitted from the host device 1, the robot control unit 25 drives the manipulator 200 of the welding robot MC1 during the bead appearance inspection such that an operation range of the welding robot MC1 defined by the main welding program is targeted. Accordingly, the sensor 4 (see FIG. 2) attached to the welding robot MC1 can move in accordance with an operation of the welding robot MC1, and can acquire input data (for example, point group data capable of specifying a three-dimensional shape of a welding bead) related to a shape of a welding bead of the workpiece Wk.

The power supply control unit 26 drives the power supply device 500 based on the main welding program generated by the main welding program creation unit 23 and a calculation result of the calculation unit 24.

Based on the execution command of the appearance inspection transmitted from the host device 1, the inspection control device 3 controls the processing of the bead appearance inspection of the workpiece or the repair workpiece produced by the main welding by the welding robot MC1. The bead appearance inspection is, for example, an inspection of whether a welding bead formed on the workpiece or the repair workpiece satisfies a predetermined welding standard (for example, a quality standard), and includes the first inspection determination and the second inspection determination described above. In order to simplify the following description, the inspection control device 3 determines whether a welding bead formed on the workpiece Wk (for example, the workpiece or the repair workpiece) satisfies the predetermined welding standard based on the input data (for example, the point group data capable of specifying the three-dimensional shape of the welding bead) related to a shape of a welding bead acquired by the sensor 4, by a comprehensive determination based on results of the first inspection determination and the second inspection determination described above. The inspection control device 3 includes at least a communication unit 30, a processor 31, a memory 32, and an inspection result storage unit 33.

The communication unit 30 is connected to the host device 1, the robot control device 2, and the sensor 4 so as to be able to communicate data with the host device 1, the robot control device 2, and the sensor 4. Although showing is simplified in FIG. 2, data is transmitted and received between a shape detection control unit 35 and the sensor 4 via the communication unit 30. The communication unit 30 receives the execution command of the bead appearance inspection transmitted from the host device 1. The communication unit 30 transmits a comprehensive determination result of the bead appearance inspections using the sensor 4 (for example, bead missing, a bead positional deviation, presence or absence of a welding defect, and a type and a position of the welding defect of the welding bead of the workpiece or the repair workpiece) to the host device 1.

The processor 31 is configured using, for example, a CPU or an FPGA, and performs various processings and controls in cooperation with the memory 32. Specifically, the processor 31 implements functions of a determination threshold storage unit 34, the shape detection control unit 35, a data processing unit 36, an inspection result determination unit 37, and a repair welding program creation unit 38 by referring to a program held in the memory 32 and executing the program.

The memory 32 includes, for example, a RAM serving as a work memory used when executing a processing of the processor 31, and a ROM for storing a program that defines the processing of the processor 31. The RAM temporarily stores data generated or acquired by the processor 31. A program that defines the processing of the processor 31 is written into the ROM. Further, the memory 32 stores data of the execution command of the bead appearance inspection of the workpiece transmitted from the host device 1, and data of the workpiece information of the workpiece generated by the main welding or the repair workpiece generated by the repair welding. Further, the memory 32 stores data of the repair welding program created by the repair welding program creation unit 38. The repair welding program is a program that defines a specific procedure (step) of the repair welding for performing correction such as repair of bead missing, a bead positional deviation, or a portion of a welding defect of a welding bead by using the welding condition in the repair welding and position information of a corresponding portion (corresponding point) on an operation trajectory of the welding robot MC1 closest to a detection point (see the above description). The program is created by the repair welding program creation unit 38, and is transmitted from the inspection control device 3 to the robot control device 2.

The inspection result storage unit 33 is configured using, for example, a hard disk or a solid state drive. The inspection result storage unit 33 stores, as an example of data generated or acquired by the processor 31, data indicating a result of the bead appearance inspection of a welding portion of the workpiece Wk (for example, the workpiece or the repair workpiece). The data indicating the result of the bead appearance inspection is generated by, for example, the inspection result determination unit 37.

The determination threshold storage unit 34 is configured with, for example, a cache memory provided in the processor 31, and stores a threshold (for example, each threshold set for each type of the welding defect) used for the processing of the bead appearance inspection by the inspection result determination unit 37 in accordance with a welding portion. The respective thresholds are, for example, allowable ranges of positional deviations of welding beads, thresholds of a length, a height, and a width of the welding bead, and thresholds of a hole, a pit, an undercut, sputtering, and a protrusion. The determination threshold storage unit 34 may store, as each threshold during the bead appearance inspection after the repair welding, an allowable range (for example, a minimum allowable value, a maximum allowable value, or the like) satisfying a minimum welding standard (quality) required by a customer or the like. Further, the determination threshold storage unit 34 may store an upper limit value of the number of times of the bead appearance inspections for each welding portion. Accordingly, in a case where a predetermined upper limit value of the number of times is exceeded when a defective portion is corrected by the repair welding, the inspection control device 3 determines that it is difficult or it is unlikely to correct the defective portion by automatic repair welding performed by the welding robot MC1, and a decrease in an operation rate of the welding system 100 can be prevented. The determination threshold storage unit 34 may further store a value indicating a range of a gray zone described later based on the above-described thresholds.

Based on the execution command of the bead appearance inspection of the welding portion of the workpiece Wk (for example, the workpiece) transmitted from the host device 1, the shape detection control unit 35 acquires the input data (for example, the point group data capable of specifying the three-dimensional shape of the welding bead) related to the shape of the welding bead transmitted from the sensor 4 while the robot control device 2 operates the welding robot MC1 to which the sensor 4 is attached based on the appearance inspection program in the bead appearance inspection. That is, the shape detection control unit 35 serves as an input unit of input data (for example, the point group data capable of specifying the three-dimensional shape of the welding bead). When the sensor 4 reaches a position where the sensor 4 can image the welding bead (in other words, a three-dimensional shape of a welding portion can be detected) in response to driving of the manipulator 200 by the robot control device 2 described above, the shape detection control unit 35 causes the sensor 4 to radiate, for example, a laser beam to acquire the input data (for example, the point group data capable of specifying the three-dimensional shape of the welding bead) related to the shape of the welding bead. When receiving the input data (see the above description) acquired by the sensor 4, the shape detection control unit 35 passes the input data to the data processing unit 36.

When acquiring the input data (see the above description) related to the shape of the welding bead from the shape detection control unit 35, the data processing unit 36 converts the input data into a data format suitable for the first inspection determination by the inspection result determination unit 37, and converts the input data into a data format suitable for the second inspection determination by the inspection result determination unit 37. The conversion of the data format may include, as a so-called preprocessing, a correction processing for removing unnecessary point group data (for example, noise) included in the input data (that is, point group data), and the above-described preprocessing may be omitted for the first inspection determination. The data processing unit 36 uses the data format suitable for the first inspection determination, and generates image data indicating the three-dimensional shape of the welding bead by executing a statistical processing on, for example, the input shape data. The data processing unit 36 may perform edge enhancement correction in which a peripheral edge portion of the welding bead is enhanced in order to enhance a position and a shape of the welding bead as data for the first inspection determination. The data processing unit 36 counts the number of times of execution of the bead appearance inspection for each portion of a welding defect, and may determine that it is difficult or it is unlikely to correct the portion of the welding defect by the automatic repair welding when a welding inspection result is not good even when the number of times of the bead appearance inspections exceeds the number of times stored in advance in the memory 32. In this case, the inspection result determination unit 37 generates an alert screen including a position of the portion of the welding defect and a type of the welding defect (for example, the hole, the pit, the undercut, the sputtering, or the protrusion), and transmits the generated alert screen to the host device 1 via the communication unit 30. The alert screen transmitted to the host device 1 is displayed on the monitor MN1. The alert screen may be displayed on the monitor MN2.

For example, the conversion of the data format suitable for the second inspection determination includes, as a so-called preprocessing, a planarization processing for converting a shape of the input data (that is, the point group data of the welding bead) into a predetermined shape (for example, a linear shape) so as to be suitable for a processing in AI (that is, a second inspection determination unit 372 to an N-th inspection determination unit 37N described later). As described above, the shape of the welding bead varies depending on a linear shape, a curved shape, presence or absence of weaving, and the like. Therefore, a learning processing of AI (for example, a neural network) capable of detecting the type of the welding defect (see the above description) for each shape becomes a very complicated processing, and is not realistic. Therefore, in the first embodiment, the AI (that is, the second inspection determination unit 372 to the N-th inspection determination unit 37N described later) can execute a learned model created by performing the learning processing in advance so as to be able to detect welding defects (see the above description) when the shape of the welding bead is, for example, the linear shape. Accordingly, the AI (that is, the second inspection determination unit 372 to the N-th inspection determination unit 37N described later) can highly accurately detect the welding defect as long as the AI inputs the point group data in which the planarization processing is performed by the data processing unit 36 and the shape of the welding bead is linearized.

The inspection result determination unit 37 can execute a total of N (N: an integer of 2 or more) types of bead appearance inspections (for example, the first inspection determination and the second inspection determination described above). Specifically, the inspection result determination unit 37 includes a first inspection determination unit 371, the second inspection determination unit 372, . . . , and the N-th inspection determination unit. In order to facilitate understanding of the description of FIG. 2, the description will be made assuming that N=2, but the same applies to an integer of N=3 or more.

Figure 5:
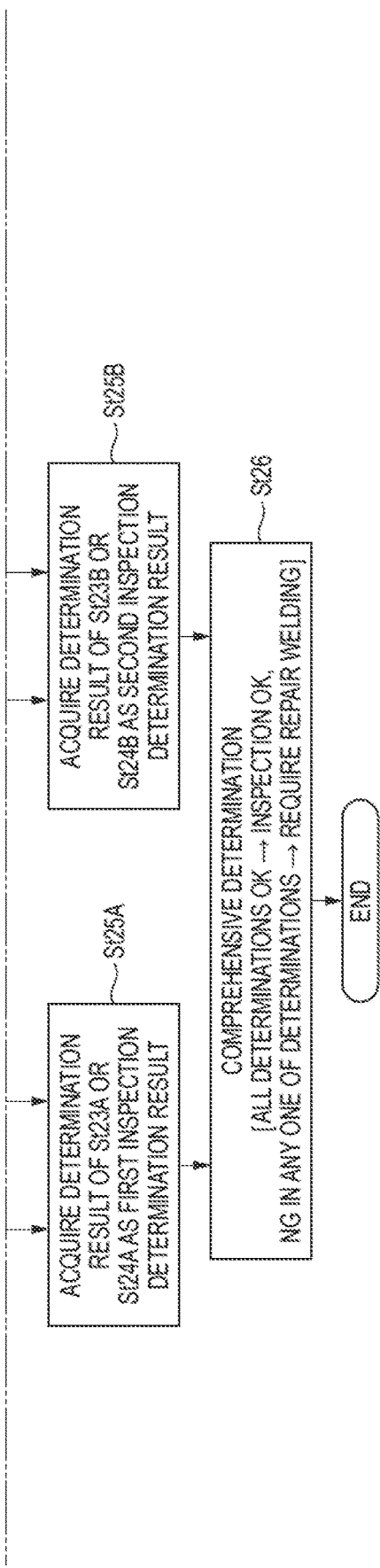
FIG. 5 is a table showing an appropriate example of the first inspection determination and the second inspection determination for each of a plurality of inspection items.

The first inspection determination unit 371 performs the first inspection determination (that is, the bead appearance inspection based on a comparison between the input data related to the shape of the welding bead acquired by the sensor 4 and the master data of the non-defective workpiece predetermined for each workpiece) by using the threshold stored in the determination threshold storage unit 34, and inspects shape reliability (for example, whether the welding bead is along a linear-shaped or curve-shaped welding line), the bead missing, and the bead positional deviation of the welding bead (see FIG. 5). FIG. 5 is a table showing an appropriate example of the first inspection determination and the second inspection determination for each of a plurality of inspection items. The first inspection determination unit 371 compares the data data-converted by the data processing unit 36 for the first inspection determination (for example, the image data generated based on the point group data) with the master data of the non-defective workpiece (so-called image processing). Therefore, as shown in FIG. 5, the first inspection determination unit 371 can highly accurately inspect the shape reliability, the bead missing, and the bead positional deviation of the welding bead. The first inspection determination unit 371 calculates an inspection score indicating an inspection result of the shape reliability, the bead missing, and the bead positional deviation of the welding bead, and creates a calculated value of the inspection score as a first inspection determination result.

The second inspection determination unit 372 to the N-th inspection determination unit 37N perform the second inspection determination (that is, a bead appearance inspection in which neural networks based on the k=(N−1) types of artificial intelligence are formed, and presence or absence of a welding defect is determined based on the AI targeting the input data related to the shape of the welding bead acquired by the sensor 4 or the input data obtained by the input data being preprocessed by the data processing unit 36), and inspect presence or absence of the hole, the pit, the undercut, and the sputtering of the welding bead (see FIG. 5). The hole, the pit, the undercut, and the sputtering of the welding bead are merely exemplified. The defective types inspected by the N-th inspection determination unit 37N are not limited thereto. When determining that a welding defect of a corresponding type is detected, each of the second inspection determination unit 372 to the N-th inspection determination unit 37N specifies a position of the welding bead where the welding defect is detected. Each of the second inspection determination unit 372 to the N-th inspection determination unit 37N determines presence or absence of each welding defect by using a learning model (AI) obtained by a learning processing for each type of a welding defect or each group of types of a welding defect in advance. Accordingly, each of the second inspection determination unit 372 to the N-th inspection determination unit 37N can highly accurately inspect, for example, presence or absence of the hole, the pit, the undercut, the sputtering, and the protrusion of the welding bead. Each of the second inspection determination unit 372 to the N-th inspection determination unit 37N does not execute the inspection of the shape reliability, the bead missing, and the bead positional deviation of the welding bead executed by the first inspection determination unit 371. The second inspection determination unit 372 to the N-th inspection determination unit 37N calculate an inspection result (in other words, an inspection score indicating an occurrence probability) of the hole, the pit, the undercut, the sputtering, and the protrusion of the welding bead, and create a calculated value of the inspection score as a second inspection determination result.

Therefore, as shown in FIG. 5, the inspection result determination unit 37 can comprehensively and highly accurately inspect presence or absence of the shape reliability, the bead missing, the bead positional deviation, the hole, the pit, the undercut, the sputtering, and the protrusion of the welding bead by selectively using and executing the first inspection determination and the second inspection determination in combination so as to be suitable for the inspection of each type of the welding defect. Although N=2 is exemplified in the above-described description, when N=3, the second inspection determination unit 372 can detect, for example, presence or absence of the hole or the pit of the welding bead as types of the welding defect by an AI, and the N-th inspection determination unit 37N (N=3) can detect, for example, presence or absence of the undercut, the sputtering, and the protrusion of the welding bead as types of the welding defect by a different AI. That is, in the second inspection determination, a plurality of AIs (learning models) may be optionally prepared such that types of the welding defect can be detected by different AIs for each combination of types of welding defects (for example, a combination of (the hole and the pit), or a combination of (the undercut, the sputtering, and the protrusion)) serving as the inspection items.

The inspection result determination unit 37 creates an appearance inspection report including the first inspection determination result created by the first inspection determination unit 371 and the second inspection determination result created by each of the second inspection determination unit 372 to the N-th inspection determination unit 37N, stores the created appearance inspection report in the memory 32, and transmits the appearance inspection report to the host device 1 via the communication unit 30. The inspection result determination unit 37 may determine whether the repair welding by the welding robot MC1 is possible (in other words, whether the repair welding by the welding robot MC1 is good or whether the repair welding by hands is good) based on an inspection score included in the first inspection determination result or the second inspection determination result described above, and may include a determination result thereof in the above-described appearance inspection report and output the determination result.

The repair welding program creation unit 38 creates a repair welding program of the workpiece Wk (for example, the workpiece or the repair workpiece) to be executed by the welding robot MC1 by using the appearance inspection report of the workpiece Wk (for example, the workpiece or the repair workpiece) by the inspection result determination unit 37 and the workpiece information (for example, information such as coordinates indicating a position of a detection point of a welding defect of the workpiece or the repair workpiece). The repair welding program may include various parameters such as the welding current, the welding voltage, the offset amount, the welding speed, and the posture of the welding torch 400 for controlling the power supply device 500, the manipulator 200, the wire feeding device 300, the welding torch 400, and the like during execution of the repair welding. The generated repair welding program may be stored in the processor 31, or may be stored in the RAM in the memory 32.

The sensor 4 is, for example, a three-dimensional shape sensor, is attached to the tip end of the welding robot MC1, is capable of acquiring a plurality of pieces of point group data capable of specifying a shape of a welding portion on the workpiece Wk (for example, the workpiece), generates point group data capable of specifying a three-dimensional shape of the welding portion based on the point group data, and transmits the generated point group data to the inspection control device 3. When the sensor 4 is not attached to the tip end of the welding robot MC1 and is disposed separately from the welding robot MC1, based on position information of the welding portion transmitted from the inspection control device 3, the sensor 4 may include a laser light source (not shown) configured to scan the welding portion on the workpiece Wk (for example, the workpiece or the repair workpiece), and a camera (not shown) that is disposed to be able to image an imaging region including a periphery of the welding portion and that images a reflection trajectory (that is, a shape line of the welding portion) of reflected laser light of laser light radiated to the welding portion. In this case, the sensor 4 transmits shape data of the welding portion based on laser light imaged by the camera (in other words, image data of the welding bead) to the inspection control device 3. The camera described above includes at least a lens (not shown) and an image sensor (not shown). The image sensor is, for example, a solid-state imaging element such as a charge coupled device (CCD) or a complementary metal oxide semi-conductor (CMOS), and converts an optical image formed on an imaging surface into an electric signal.

(Operation of Welding System)

Figure 3:
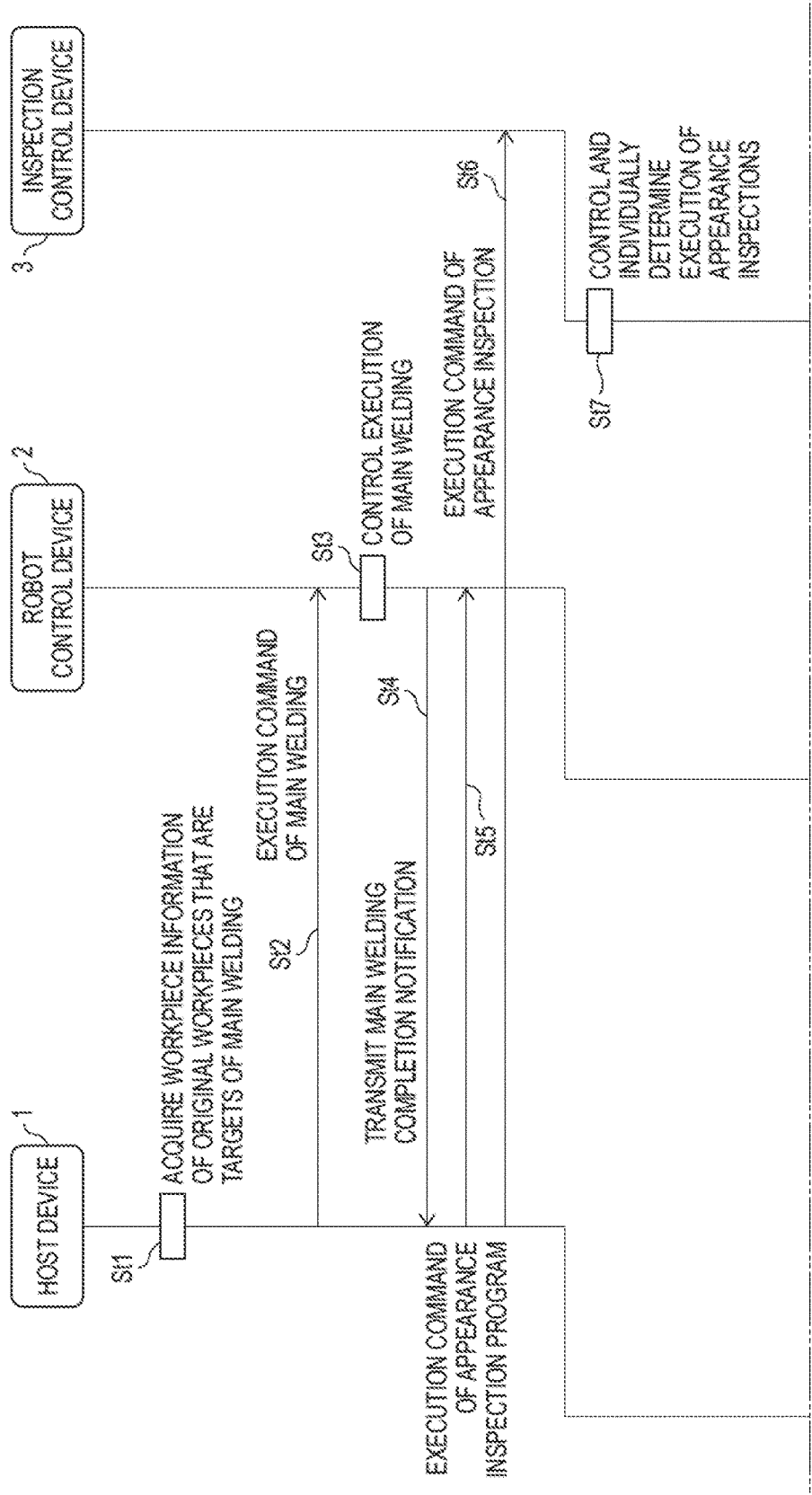
FIG. 3 is a sequence diagram showing an example of a series of processing procedures including main welding, a bead appearance inspection, and repair welding by a welding system according to the first embodiment.

Next, a series of operation procedures of the main welding, the bead appearance inspection, and the repair welding by the welding system 100 according to the first embodiment will be described with reference to FIG. 3. FIG. 3 is a sequence diagram showing an example of the series of processing procedures including the main welding, the bead appearance inspection, and the repair welding by the welding system 100 according to the first embodiment. In description of FIG. 3, an operation procedure performed among the host device 1, the robot control device 2, and the inspection control device 3 in each step of the main welding using a plurality of original workpieces and the repair welding performed based on a fact that the bead appearance inspection of the workpiece fails (that is, a comprehensive determination result indicating that there is a welding defect) will be described as an example.

In FIG. 3, the host device 1 acquires workpiece information (for example, IDs, names, and welding portions of the original workpieces) of the original workpieces that are targets of the main welding (St1), and generates an execution command of the main welding including the workpiece information of the original workpieces. The host device 1 transmits the execution command of the main welding including the workpiece information of the original workpieces to the robot control device 2 (St2). The robot control device 2 may execute the processings of steps St1 and St2 without using the host device 1. In this case, it is preferable that data the same as data stored in the external storage ST is stored in the memory 22 of the robot control device 2, or the robot control device 2 is connected such that data can be acquired from the external storage ST.

When receiving the execution command of the main welding transmitted from the host device 1, by using the workpiece information of the plurality of original workpieces included in the execution command, the robot control device 2 creates a main welding program of the main welding executed by the welding robot MC1, and causes the welding robot MC1 to execute the main welding in accordance with the main welding program (St3). When determining by various known methods that the main welding by the welding robot MC1 is completed, the robot control device 2 generates a main welding completion notification indicating that the main welding is completed, and transmits the generated main welding completion notification to the host device 1 (St4). When receiving the main welding completion notification, the host device 1 generates an execution command of an appearance inspection program including an appearance inspection program of the workpiece and transmits the generated execution command to the robot control device 2 (St5), and generates an execution command of a bead appearance inspection of the workpiece and transmits the generated execution command to the inspection control device 3 (St6). The robot control device 2 executes the appearance inspection program received from the host device 1 at the start of the bead appearance inspection, and moves the sensor 4 attached to the welding robot MC1 along a welding line (St7). The sensor 4 acquires point group data capable of specifying a three-dimensional shape of the workpiece while a welding portion of the workpiece is moved by the robot control device 2 in a scannable manner (St7).

The inspection control device 3 uses the point group data capable of specifying the three-dimensional shape of the welding bead acquired by the sensor 4 as input data, and individually (in parallel) executes the first inspection determination and the second inspection determination described above (St7). The inspection control device 3 performs a comprehensive determination of the bead appearance inspections of the welding bead of the workpiece based on results of the individual bead appearance inspections (that is, the first inspection determination and the second inspection determination) in step St7 (St8).

As a result of the comprehensive determination in step St8, when determining that the repair welding is necessary because there is a welding defect in the workpiece (St9), the inspection control device 3 acquires the main welding program from the robot control device 2, and creates a repair welding program by modifying a part of the main welding program (St9). The modified part is, for example, content indicating a portion (range) where the repair welding is performed. Further, although detailed showing is omitted in FIG. 3, the inspection control device 3 may request data of the main welding program from the robot control device 2 in step St9, and may acquire the data of the main welding program transmitted from the robot control device 2 in response to the request, or may acquire the data of the main welding program transmitted from the robot control device 2 in advance after step St3. Accordingly, the inspection control device 3 can efficiently create the data of the repair welding program by partially modifying the data of the main welding program acquired from the robot control device 2. The inspection control device 3 generates an appearance inspection report including the result of the comprehensive determination in step St8 and the repair welding program, and transmits the generated appearance inspection report to the robot control device 2 (St10). Further, the inspection control device 3 also transmits the appearance inspection report generated in the same manner to the host device 1 (St11).

Upon receiving the appearance inspection report in step St11, the host device 1 generates an execution command of the repair welding targeting the workpiece, and transmits the generated execution command to the robot control device 2 (St12). When receiving the execution command of the repair welding transmitted from the host device 1, the robot control device 2 causes the welding robot MC1 to execute the repair welding in accordance with the repair welding program based on the repair welding program (received in step St10) targeting a workpiece designated in the execution command (St13). When determining by various known methods that the repair welding by the welding robot MC1 is completed, the robot control device 2 transmits workpiece information of the repair workpiece (for example, an ID of the repair workpiece, workpiece information including IDs of the plurality of original workpieces used in the main welding (for example, IDs and names of the original workpieces, and welding portions of the original workpieces), and welding conditions during execution of the main welding and the repair welding) to the host device 1 (St14).

Upon receiving the workpiece information including the ID of the repair workpiece transmitted from the robot control device 2, the host device 1 sets a management ID suitable for a user corresponding to the ID of the repair workpiece, and stores data indicating that welding of the repair workpiece corresponding to the management ID is completed in the external storage ST (St15).

Figure 4:
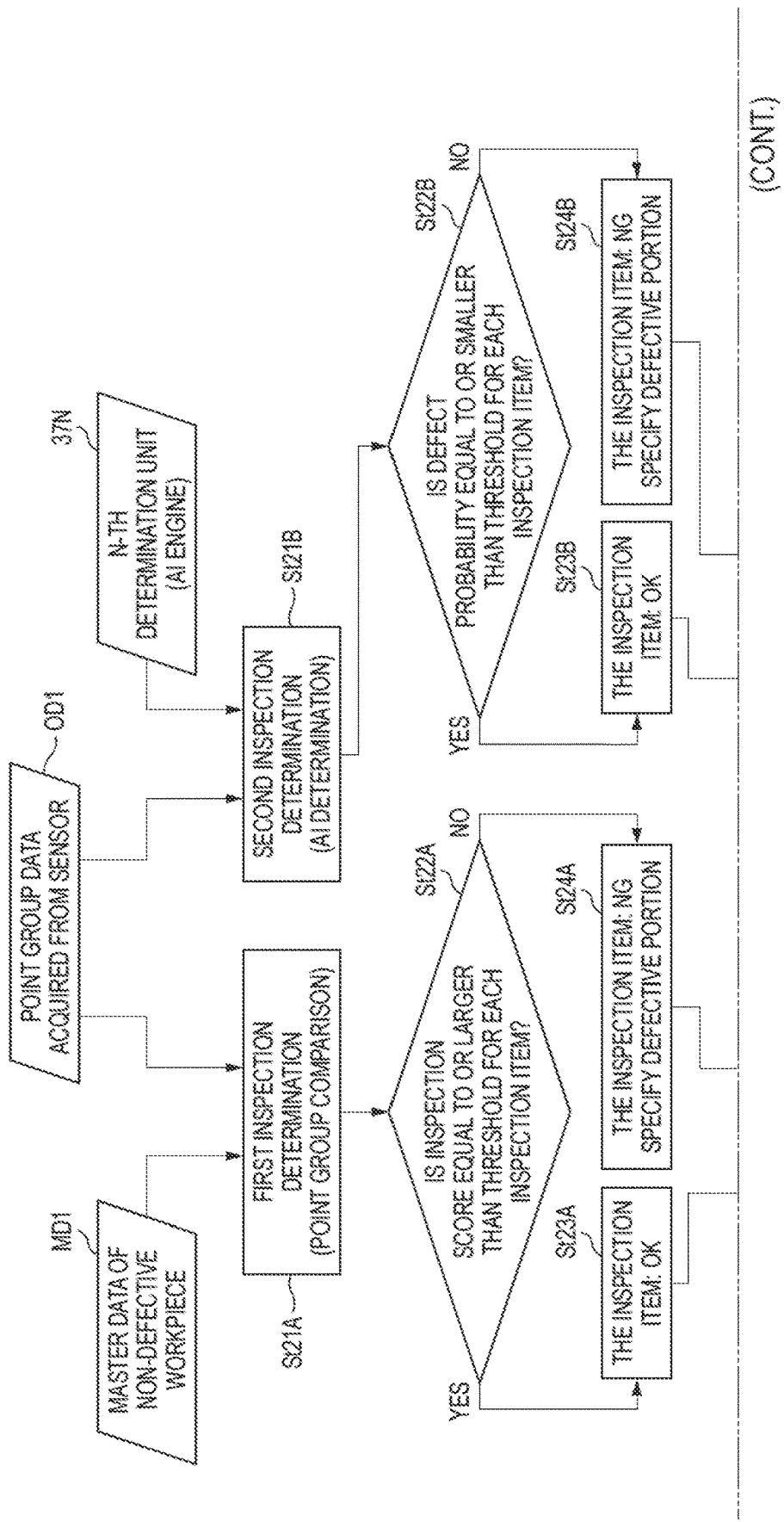
FIG. 4 is a flowchart showing an example of a processing procedure showing details of a first inspection determination (point group comparison) and second to N-th inspection determinations (AI determination).

Next, details of the individual inspections in step St7 and the comprehensive determination in step St8 in FIG. 3 will be described with reference to FIG. 4. FIG. 4 is a flowchart showing an example of a processing procedure showing details of the first inspection determination (point group comparison) and the second to N-th inspection determinations (AI determination). In order to facilitate understanding of the description in FIG. 4, N=2.

In FIG. 4, point group data OD1 capable of specifying a three-dimensional shape of a welding bead acquired by the sensor 4 is used for both the first inspection determination and the second inspection determination. The data processing unit 36 converts the point group data OD1 from the sensor 4 into a data format suitable for the first inspection determination (for example, image data showing the three-dimensional shape of the welding bead), and passes the point group data OD1 to the first inspection determination unit 371. The first inspection determination unit 371 reads master data MD1 of a non-defective workpiece (for example, image data showing an ideal three-dimensional shape of a welding bead of the non-defective workpiece) stored in the memory 32 from the memory 32, and executes the first inspection determination of comparing the image data from the data processing unit 36 with the master data MID (St21A).

The first inspection determination unit 371 determines whether an inspection score calculated for each inspection item (for example, the shape reliability, the bead missing, and the bead positional deviation) is equal to or larger than a threshold set in advance for each inspection item (St22A). That is, the first inspection determination unit 371 determines whether an inspection score of the shape reliability is equal to or larger than a shape reliability threshold, whether an inspection score related to presence or absence of the bead missing is equal to or larger than a bead missing threshold, and whether an inspection score related to presence or absence of the bead positional deviation is equal to or larger than a bead positional deviation threshold by comparing the image data based on the point group data OD1 with the master data MD1 (St22A). When determining that the inspection scores equal to or larger than the shape reliability threshold, the bead missing threshold, and the bead positional deviation threshold are obtained (St23A, YES), the first inspection determination unit 371 determines that the inspection items are "OK" (that is, the shape reliability is satisfied, and the bead missing or the bead positional deviation is not detected) (St23A). In contrast, when determining that the inspection scores less than the shape reliability threshold, the bead missing threshold, and the bead positional deviation threshold are obtained (St23A, NO), the first inspection determination unit 371 determines that the inspection items are "NG" (that is, the shape reliability is insufficient or the bead missing or the bead positional deviation is detected) (St24A). The first inspection determination unit 371 acquires a determination result of step St23A or step St24A as the first inspection determination result (St25A).

The N-th inspection determination unit 37N determines whether a defect probability value (that is, an inspection score) that is an output value of an AI engine (for example, a neural network) for each inspection item (for example, the hole, the pit, the undercut, the sputtering, and the protrusion) is equal to or smaller than a threshold set in advance for each inspection item (St22B). That is, the N-th inspection determination unit 37N determines whether the defect probability value calculated for each inspection item by the AI engine to which the point group data OD1 is input is equal to or smaller than a hole detection threshold, a pit detection threshold, an undercut detection threshold, a sputtering detection threshold, or a protrusion detection threshold (St22B). When determining that the output value (defect probability value) of the AI engine for each inspection item is equal to or smaller than the hole detection threshold, the pit detection threshold, the undercut detection threshold, the sputtering detection threshold, or the protrusion detection threshold (St23B, YES), the N-th inspection determination unit 37N determines that the inspection item is "OK" (that is, none of the hole, the pit, the undercut, the sputtering, and the protrusion is detected)(St23B). In contrast, when determining that the output value (defect probability value) of the AI engine for each inspection item is equal to or larger than the hole detection threshold, the pit detection threshold, the undercut detection threshold, the sputtering detection threshold, or the protrusion detection threshold (St23B, NO), the first inspection determination unit 371 determines that the inspection item is "NG" (that is, any one of the hole, the pit, the undercut, the sputtering, and the protrusion is detected) (St24B). The N-th inspection determination unit 37N acquires a determination result of step St23B or step St24B as the second inspection determination result (St25B).

The inspection result determination unit 37 performs the comprehensive determination of the bead appearance inspections by using the first inspection determination result obtained in step St25A and the second inspection determination result obtained in step St25B (St26). For example, when determining that both the first inspection determination result and the second inspection determination result have obtained a result indicating that there is no welding defect, the inspection result determination unit 37 determines that the bead appearance inspection is passed (in other words, the repair welding is not necessary). In contrast, when determining that either the first inspection determination result or the second inspection determination result has obtained a result indicating that any one of the welding defects is detected, the inspection result determination unit 37 determines that the bead appearance inspection fails (in other words, the repair welding for repairing the detected welding defect is necessary).

As described above, in the welding system 100 according to the first embodiment, the inspection control device 3 that is an example of the bead appearance inspection device inputs the input data (for example, the point group data OD1) related to the welding bead of the workpiece produced by welding to the processor 31. The inspection control device 3 uses the input data and the master data MD1 of the non-defective workpiece to perform the first inspection determination of the welding bead by the first inspection determination unit 371 based on the comparison between the input data and the master data MD1, and is equipped with k (k: an integer of 1 or more) types of artificial intelligence, and performs the second inspection determination of the welding bead by the second inspection determination unit 372 to the N-th inspection determination unit 37N based on the processings of the k types of artificial intelligence targeting the input data. k=(N−1), and the same applies to the following. The inspection control device 3 outputs the results of the bead appearance inspections of the welding bead to the output device (for example, the monitor MN2) in the inspection result determination unit 37 based on the determination results of the first inspection determination unit 371 and the second inspection determination unit 372 to the N-th inspection determination unit 37N.

Accordingly, the inspection control device 3 can execute the first inspection determination based on the comparison between the input data indicating the three-dimensional shape of the welding bead and the master data MD1 and the second inspection determination for detecting presence or absence of the welding defect of the welding bead based on the AI processing in combination. Therefore, the appearance inspection of the welding bead of the workpiece produced by the main welding can be performed more efficiently. Particularly, when presence or absence of the welding defect is detected by the AI processing, it is possible to prepare k (=(N−1)) types of different AIs in accordance with an inspection item that is a target of the bead appearance inspection of the user. Therefore, the inspection control device 3 can improve convenience for the user of the appearance inspection of the welding bead.

The appearance inspection item of the welding bead that is a target of the first inspection determination and the appearance inspection item of the welding bead that is a target of the second inspection determination are different. Accordingly, the inspection control device 3 can comprehensively inspect the appearance inspection item of the welding bead highly accurately detected by the first inspection determination and the appearance inspection item of the welding bead highly accurately detected by the second inspection determination.

When k is an integer of 2 or more, the appearance inspection items of the welding bead that is the target of the second inspection determination executed by the second inspection determination unit 372 to the N-th inspection determination unit 37N (in other words, an example of k second inspection determination units) are different. For example, the second inspection determination unit 372 detects presence or absence of the hole and the sputtering of the welding bead, and the N-th inspection determination unit 37N detects presence or absence of the pit and the undercut of the welding bead. Accordingly, since the inspection control device 3 can provide a plurality of combinations of the second inspection determinations that can be highly accurately detected by the AI processing for each inspection item, the inspection control device 3 can highly accurately inspect presence or absence of each type of welding defect of the welding bead as compared with a case where a large number of inspection items are inspected by, for example, one type of AI processing.

The inspection control device 3 communicates with the welding robot MC1 capable of executing the repair welding targeting the welding bead of the workpiece. When determining that any one of the appearance inspection items of the determination results of the first inspection determination unit 371 and k second determination units (the second inspection determination unit 372 to the N-th inspection determination unit 37N) has a defect, the inspection control device 3 transmits, to the welding robot MC1, the execution instruction of the repair welding for correcting the corresponding portion of the welding bead determined to have the defect. Accordingly, when determining that a welding defect is detected in any one of the inspection items as the comprehensive determination based on results of the first inspection determination and the second inspection determination, the inspection control device 3 can instruct the welding robot MC1 to perform the repair welding for automatically correcting, by the welding robot MC1, the inspection item in which the welding defect has occurred, and can rapidly and smoothly increase degree of completion of the workpiece.

The inspection control device 3 converts the input data into a data format suitable for input to k types of artificial intelligence. Accordingly, the inspection control device 3 can improve accuracy of the AI processings executed by the second inspection determination unit 372 to the N-th inspection determination unit 37N, and can improve detection accuracy of presence or absence of the welding defect (for example, the hole, the pit, the undercut, and the sputtering) of the welding bead.

The appearance inspection item of the welding bead that is the target of the first inspection determination includes the shape of the welding bead, the missing of the welding bead, and the positional deviation of the welding bead. The appearance inspection item of the welding bead that is the target of the second inspection determination includes the hole, the pit, the undercut, the sputtering, and the protrusion of the welding bead. Accordingly, the inspection control device 3 can comprehensively inspect the appearance inspection item (for example, the shape of the welding bead, the missing of the welding bead, and the positional deviation of the welding bead) of the welding bead detected highly accurately by the first inspection determination, and the appearance inspection item (for example, the hole, the pit, the undercut, the sputtering, and the protrusion of the welding bead) of the welding bead detected highly accurately by the second inspection determination.

Second Embodiment

In the first embodiment, both the first inspection determination and the second inspection determination are executed by the inspection control device 3. In a second embodiment, an example in which a first inspection determination and a second inspection determination are executed by different devices will be described. Hereinafter, it will be described that the first inspection determination is executed by the inspection control device 3, and the second inspection determination is executed by the host device 1. However, the second inspection determination may also be executed by another device other than the host device 1.

(Configuration of Welding System)

Figure 6:
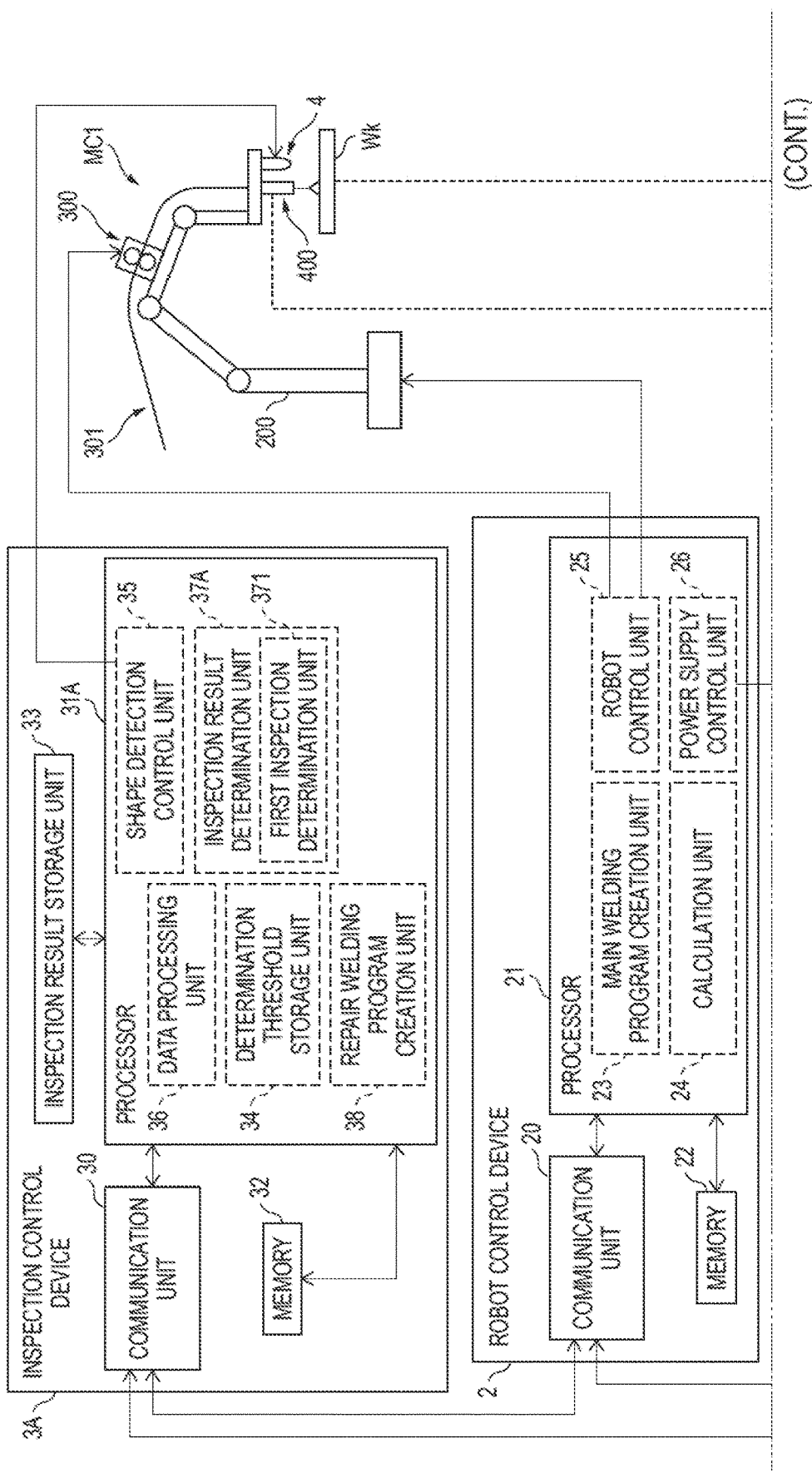
FIG. 6 is a diagram showing an internal configuration example of an inspection control device, the robot control device, and a host device according to a second embodiment.

FIG. 6 is a diagram showing an internal configuration example of an inspection control device 3A, the robot control device 2, and a host device 1A according to the second embodiment. In description of FIG. 6, the same reference numerals are assigned to those having the same configuration as parts of FIG. 2, description thereof will be simplified or omitted, and different content will be described. Further, a configuration of a welding system 100A according to the second embodiment is the same as that of the welding system 100 according to the first embodiment (see FIG. 1).

The welding system 100A that is an example of a bead appearance inspection system includes the host device 1A connected to the external storage ST, the input interface UI1, and the monitor MN1, the robot control device 2, the inspection control device 3A, the sensor 4, the main welding robot MC1a, and the repair welding robot MC1b.

In the inspection control device 3A that is an example of the bead appearance inspection device, a processor 31A includes the determination threshold storage unit 34, the shape detection control unit 35, the data processing unit 36, an inspection result determination unit 37A, and the repair welding program creation unit 38. The inspection result determination unit 37A only includes the first inspection determination unit 371. Since the configuration of the first inspection determination unit 371 is similar to that of the first embodiment, description thereof will be omitted.

In the host device 1A that is an example of the bead appearance inspection device, a processor 11A includes the cell control unit 13, a second inspection determination unit 142 to an N-th inspection determination unit 14N. Similar to the second inspection determination unit 372 to the N-th inspection determination unit 37N, the second inspection determination unit 142 to the N-th inspection determination unit 14N perform the second inspection determination (that is, a bead appearance inspection in which a neural network based on k=(N−1) types of artificial intelligence is formed, and presence or absence of a defective portion of welding is determined based on an AI targeting input data related to a shape of a welding bead acquired by the sensor 4), and inspect presence or absence of a hole, a pit, an undercut, sputtering, and a protrusion of the welding bead (see FIG. 5). The memory 12 or the processor 11A may perform a function similar to that of the determination threshold storage unit 34 of the inspection control device 3A. Although showing is omitted, the determination threshold storage unit may be provided in the processor 11A.

(Operation of Welding System)

Figure 7:
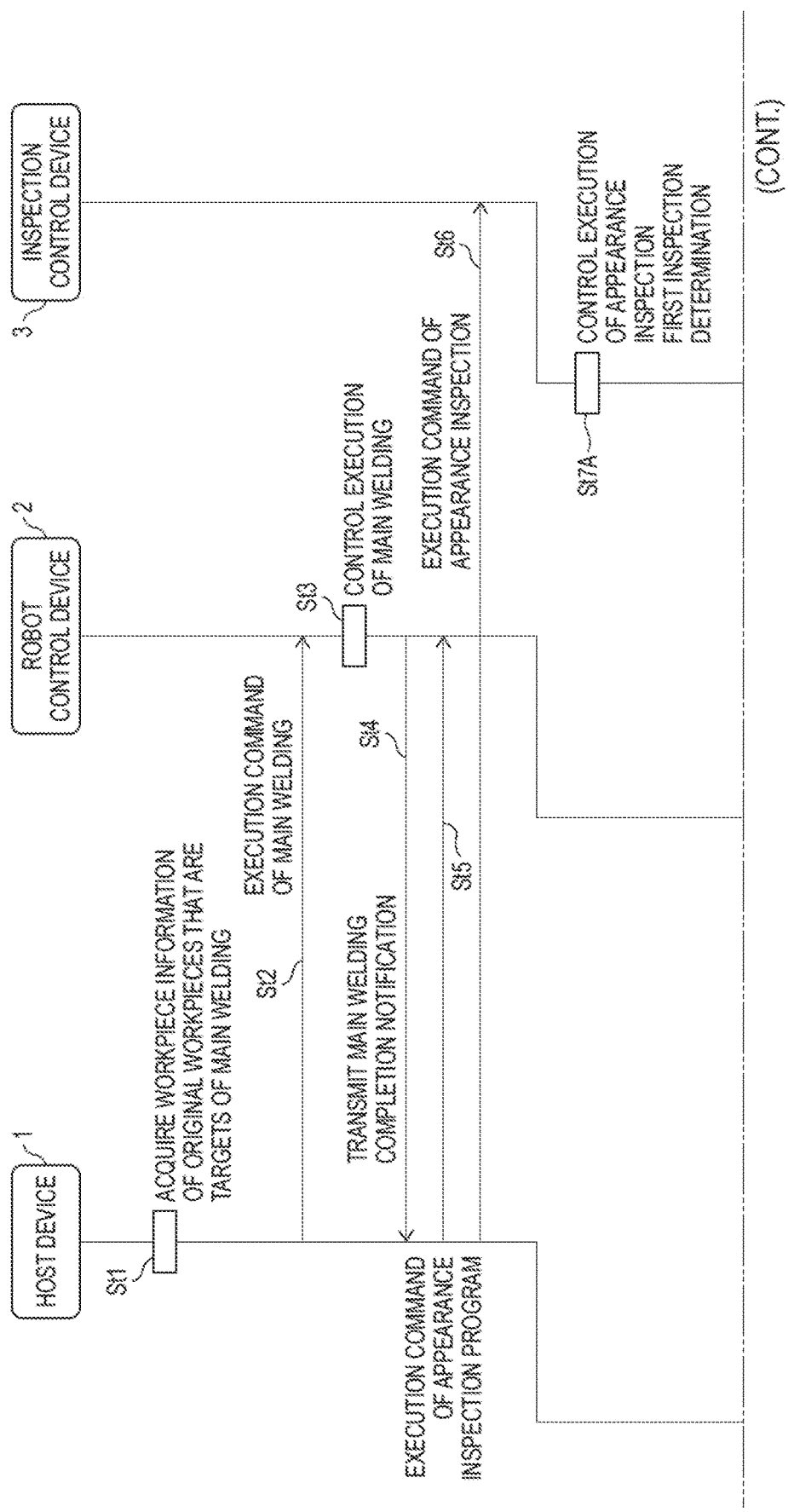
FIG. 7 is a sequence diagram showing an example of a series of processing procedures including main welding, a bead appearance inspection, and repair welding by a welding system according to the second embodiment.

Next, a series of processing procedures including main welding, the bead appearance inspection, and repair welding by the welding system 100A according to the second embodiment will be described with reference to FIG. 7. FIG. 7 is a sequence diagram showing an example of the series of processing procedures including the main welding, the bead appearance inspection, and the repair welding by the welding system 100A according to the second embodiment. In description of FIG. 7, an operation procedure performed among the host device 1A, the robot control device 2, and the inspection control device 3A in each step of the main welding using a plurality of original workpieces and the repair welding performed based on a fact that the bead appearance inspection of the workpiece fails will be described as an example. Further, in description of FIG. 7, the same step numbers are assigned to the same processings as those in FIG. 3, description thereof will be simplified or omitted, and different content will be described.

In FIG. 7, after step St6, the robot control device 2 executes an appearance inspection program received from the host device 1A at the start of the bead appearance inspection, and moves the sensor 4 attached to the welding robot MC1 along a welding line (St7A). The sensor 4 acquires point group data capable of specifying a three-dimensional shape of a workpiece while a welding portion of the workpiece is moved by the robot control device 2 in a scannable manner (St7A). The inspection control device 3A uses point group data capable of specifying a three-dimensional shape of a welding bead acquired by the sensor 4 as input data, and executes the above-described first inspection determination (St7A). Further, the inspection control device 3A generates an execution instruction of the above-described second inspection determination by the processor 31A, and transmits the generated execution instruction to the host device 1A (St31).

When receiving the execution instruction of the second inspection determination transmitted from the inspection control device 3A in step St31, the host device 1A executes the second inspection determination by the second inspection determination unit 142 to the N-th inspection determination unit 14N based on the execution instruction (St32). Since details of the second inspection determination executed in step St32 are the same as those of content described in the first embodiment, description thereof will be omitted. The host device 1A generates a processing result of the second inspection determination (that is, detection of presence or absence of a welding defect for each inspection item by an AI processing) and transmits the generated processing result to the inspection control device 3A (St33). The inspection control device 3A performs a comprehensive determination of bead appearance inspections of the workpiece based on results of the first inspection determination by the inspection control device 3 in step St7 and the second inspection determination by the host device 1A in step St32 (St8A). Since details of the comprehensive determination executed in step St8A are the same as those of content described in the first embodiment, description thereof will be omitted. Since processings after step St8A are the same as those in FIG. 3, description thereof will be omitted.

As described above, the welding system 100A, which is an example of the bead appearance inspection system according to the second embodiment, inputs the input data (for example, the point group data OD1) related to the welding bead of the workpiece produced by welding to the inspection control device 3A. The welding system 100A uses the input data and the master data MD1 of a non-defective workpiece, and performs the first inspection determination of the welding bead by the inspection control device 3A based on a comparison between the input data and the master data MD1, and is equipped with k (k: an integer of 1 or more) types of artificial intelligence, and performs the second inspection determination of the welding bead by the second inspection determination unit 142 to the N-th inspection determination unit 14N of the host device 1A based on processings of the k types of artificial intelligence targeting the input data. The inspection control device 3A outputs a result of the bead appearance inspection of the welding bead to an output device (for example, the monitor MN2) in the inspection result determination unit 37 based on determination results of the first inspection determination unit 371 of the inspection control device 3A and the second inspection determination unit 142 to the N-th inspection determination unit 14N of the host device 1A.

Accordingly, the welding system 100A can perform the first inspection determination by the inspection control device 3A based on the comparison between the input data indicating the three-dimensional shape of the welding bead and the master data MD1, and can execute the second inspection determination for detecting presence or absence of a welding defect of the welding bead by the host device 1A based on the AI processing in a distributed manner. Therefore, the welding system 100A can suppress a processing load of the bead appearance inspection as compared with a case where both the first inspection determination and the second inspection determination are executed only by the inspection control device 3 as in, for example, the first embodiment. Further, the welding system 100A can more efficiently perform the appearance inspection of the welding bead of the workpiece produced by the main welding. Particularly, when presence or absence of the welding defect is detected by the AI processing, it is possible to prepare k (=(N−1)) types of different AIs in accordance with an inspection item that is a target of the bead appearance inspection of the user. Therefore, the welding system 100A can improve convenience for the user of the appearance inspection of the welding bead.

(Gray Zone Setting when Performing Determination Using Thresholds)

Figure 8:
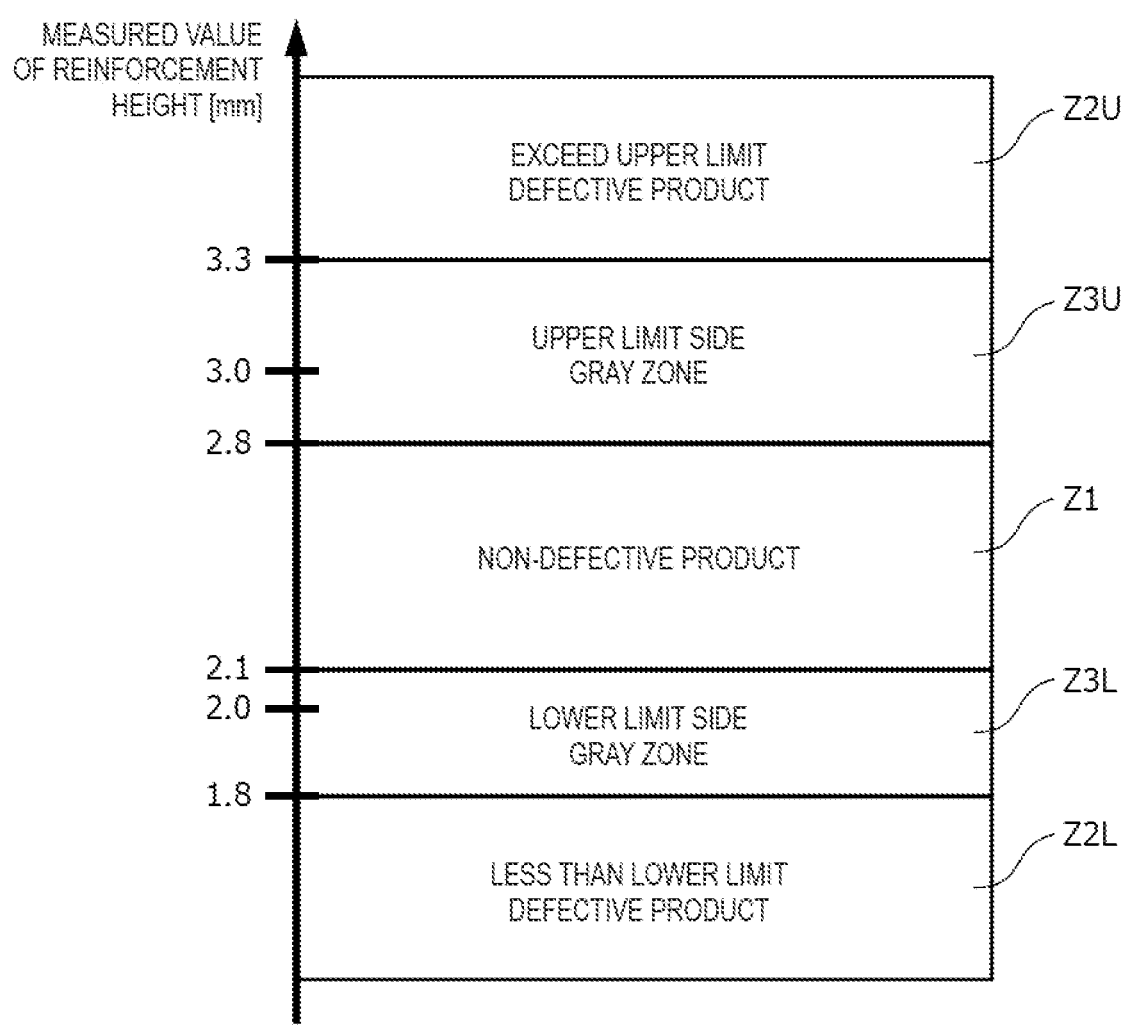
FIG. 8 is a conceptual diagram showing a first gray zone setting example of the bead appearance inspection.

Next, setting of the gray zone when performing a determination using the thresholds in the bead appearance inspection will be described. FIG. 8 is a conceptual diagram showing a first gray zone setting example of the bead appearance inspection. The determination using the thresholds can be performed in the first inspection determination (see step St21A in FIG. 4) and in the second to N-th inspection determinations (see step St21B in FIG. 4). Here, a setting example of the gray zone for an appearance inspection item "reinforcement height" in the first inspection determination is shown. However, the setting of the gray zone can be similarly performed for other appearance inspection items, and the setting of the gray zone can be similarly performed not only in the first inspection determination but also in the second to N-th inspection determinations.

It is assumed that a reinforcement height of the non-defective workpiece is from 2.0 mm (lower limit threshold) to 3.0 mm (upper limit threshold). 2.0 mm and 3.0 mm are thresholds for non-defective product/defective product determination. The bead appearance inspection device (the host device 1, the inspection control device 3, or the like) can determine whether a welding result is non-defective/ defective by comparing a value obtained from the input data (the point group data OD1) (for example, a measured value of the reinforcement height, a measured value indicating a diameter of the hole, a value of a standard deviation of measured values, a score for determination, or the like) with the thresholds. For example, the bead appearance inspection device can determine that a workpiece is a non-defective product when the measured value of the reinforcement height is between 2.0 mm and 3.0 mm, and a workpiece is a defective product when the measured value of the reinforcement height is less than 2.0 mm or exceeds 3.0 mm. In the present example, two thresholds including the upper limit threshold of 3.0 mm and the lower limit threshold of 2.0 mm are set. However, only one threshold may be set, and it is possible to determine a non-defective product or a defective product based on whether the measured value, the score, or the like exceeds the thresholds.

Here, since a quality standard may be different for each user and it is also necessary to comprehensively consider characteristics of the workpiece and the like, it is not easy to determine an optimum threshold for determination. For example, a certain user may determine that a welded workpiece having a welding bead with a reinforcement height of 1.9 mm is a non-defective product. Another user may determine that a welded workpiece having a welding bead with a reinforcement height of 2.01 mm is a defective product. Therefore, it is not easy to specify an optimum threshold value that can be generally used.

Therefore, in the present embodiment, a gray zone region is provided between a region determined to be a non-defective product and a region determined to be a defective product. In the first gray zone setting example shown in FIG. 8, for the upper limit threshold, a gray zone Z3U having a reinforcement height of 2.8 mm to 3.3 mm is provided between a non-defective product zone Z1 having a reinforcement height of 2.8 mm or less and a defective product zone Z2U having a reinforcement height of more than 3.3 mm. Similarly, in the first gray zone setting example shown in FIG. 8, for the lower limit threshold, a gray zone Z3L having a reinforcement height of 1.8 mm to 2.1 mm is provided between a non-defective product zone Z1 having a reinforcement height of more than 2.1 mm and a defective product zone Z2L having a reinforcement height of less than 1.8 mm.

As in the example described above, the gray zone Z3U or Z3L is provided between the non-defective product zone Z1 determined to be a non-defective product and the defective product zone Z2U or Z2L determined to be a defective product. Then, when a value (for example, the measured value of the reinforcement height) obtained from the input data (the point group data OD1) is within the gray zone (gray determination is made), a workpiece having a welding bead determined to be gray is visually checked by the user or precisely rechecked. Accordingly, determination accuracy of the appearance inspection of the workpiece in a boundary region between the non-defective product and the defective product can be improved, and situations such as overlooking a defective product and erroneously detecting a non-defective product as a defective product can be avoided. Therefore, productivity of a product on which welding is performed can be enhanced.

The thresholds can also beset for inspection items other than the reinforcement height. For example, the thresholds can also be set for a width of the bead, a depth of the undercut, the number of pits generated in the bead, and the like. Further, for the hole, a score based on a size of the hole and the number of holes may be calculated, and thresholds for the score may be set. The threshold(s) may include both the upper limit threshold and the lower limit threshold, or may include only any one of the upper limit threshold and the lower limit threshold.

The gray zone may be designated as a range based on a relative value with respect to a threshold. For example, when the threshold is 2.0 mm, a range from 1.8 mm to 2.3 mm, which indicates a range from 0.2 mm below the threshold to 0.3 mm above the threshold, may be set as the gray zone. However, the range of the gray zone may be designated based on an absolute value instead of the relative value with respect to the threshold.

The gray zone may be set as a width centered on a threshold. For example, when the threshold is 2.0 mm and the width is 0.5 mm, a range from 1.5 mm to 2.5 mm may be set as the gray zone.

A unit used for designating the range of the gray zone may not necessarily be the same unit as that of the measured value. For example, when the measured value of the inspection item "reinforcement height" is measured in a unit of"mm", the range of the gray zone may be designated in a unit other than "mm", such as "from 0.8 times to 1.2 times the threshold". The standard deviation of the measured values may be calculated in advance based on a production result of a past product, and the range of the gray zone may be set based on a value of the standard deviation.

Whether the gray zone is provided or not may be set separately for the upper limit threshold and the lower limit threshold. For example, setting may be performed such that the gray zone is provided for the upper limit threshold, and the gray zone is not provided for the lower limit threshold.

Figure 9:
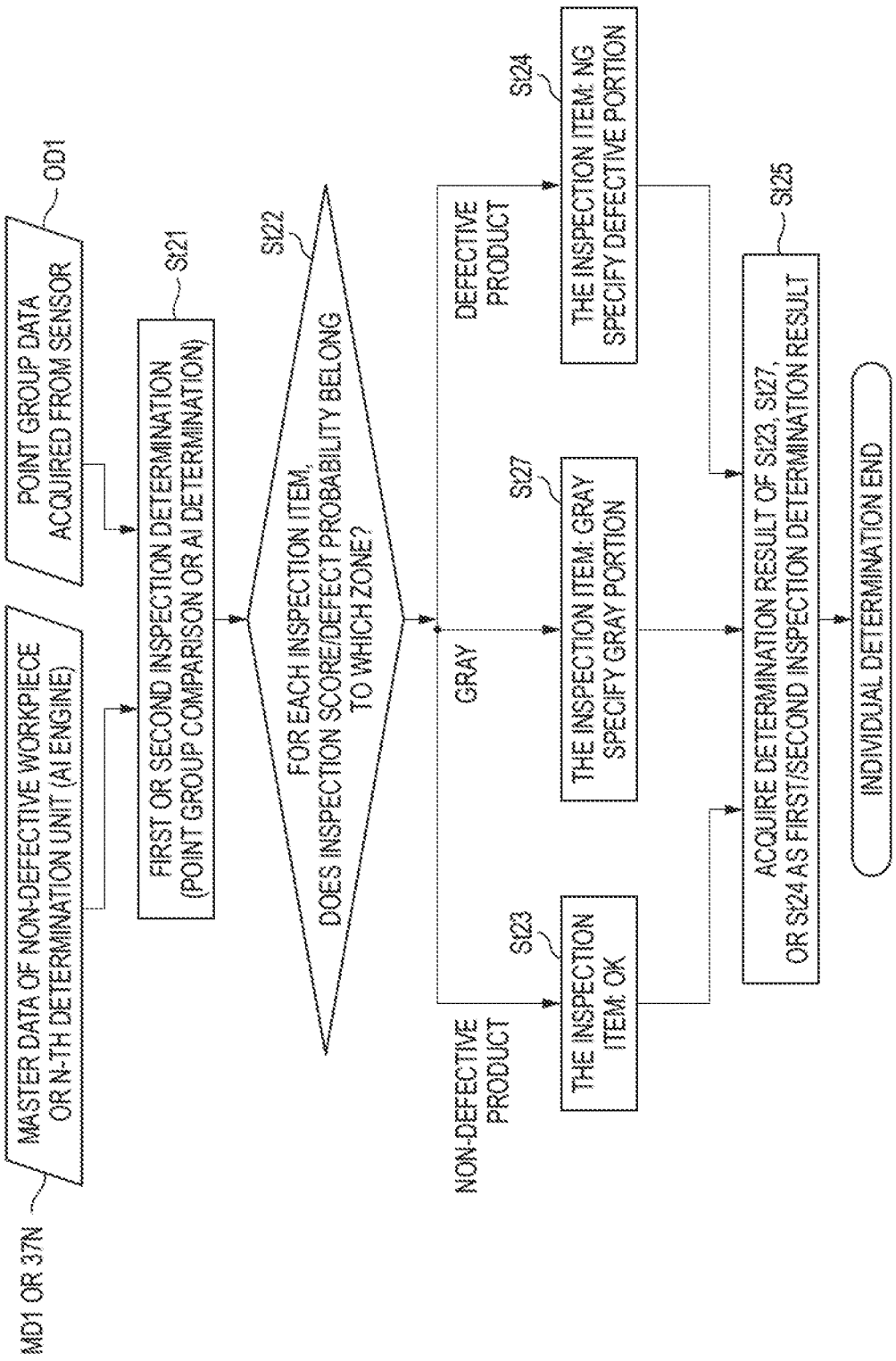
FIG. 9 is a flowchart showing an example of a processing procedure of an individual determination in the bead appearance inspection according to the first gray zone setting example of the bead appearance inspection.

FIG. 9 is a flowchart showing an example of a processing procedure of an individual determination in the bead appearance inspection according to the first gray zone setting example of the bead appearance inspection. The flowchart shown in FIG. 9 corresponds to both the first inspection determination (steps St21A to St25A) and the second inspection determination (steps St21B to St25B) shown in FIG. 4. The processing shown in FIG. 9 is similar when the processor 31 performs both the first inspection determination and the second inspection determination (see FIG. 3) and when the processor 31A performs the first inspection determination and the processor 11A performs the second inspection determination (see FIG. 7). Therefore, for convenience of description, the following description will be made assuming that a subject of the processing is a "processor".

The processor performs the first inspection determination (point group comparison) or the second inspection determination (AI determination) described above (St21). The processor determines, for each inspection item, which of the non-defective product zone (Z1), the gray zone (Z3U. Z3L), and the defective product zone (Z2U, Z2L) for the inspection item, a value of the inspection score (in the case of the first inspection determination) or the defect probability (in the case of the second inspection determination) belongs to (St22). The inspection score and the defect probability are values obtained from the input data (point group data OD1).

When determining that the value of the inspection score or the defect probability belongs to the non-defective product zone (Z1), the processor determines that the inspection item is "OK" (St23). When determining that the value of the inspection score or the defect probability belongs to the defective product zone (Z2U. Z2L), the processor determines that the inspection item is "NG" (St24). When determining that the value of the inspection score or the defect probability belongs to the gray zone (Z3U, Z3L), the processor determines that the inspection item is "gray" (St27).

The processor acquires a determination result of step St23A, step St24, or step St27 as the first inspection determination result or the second inspection determination result (St25).

Figure 10:
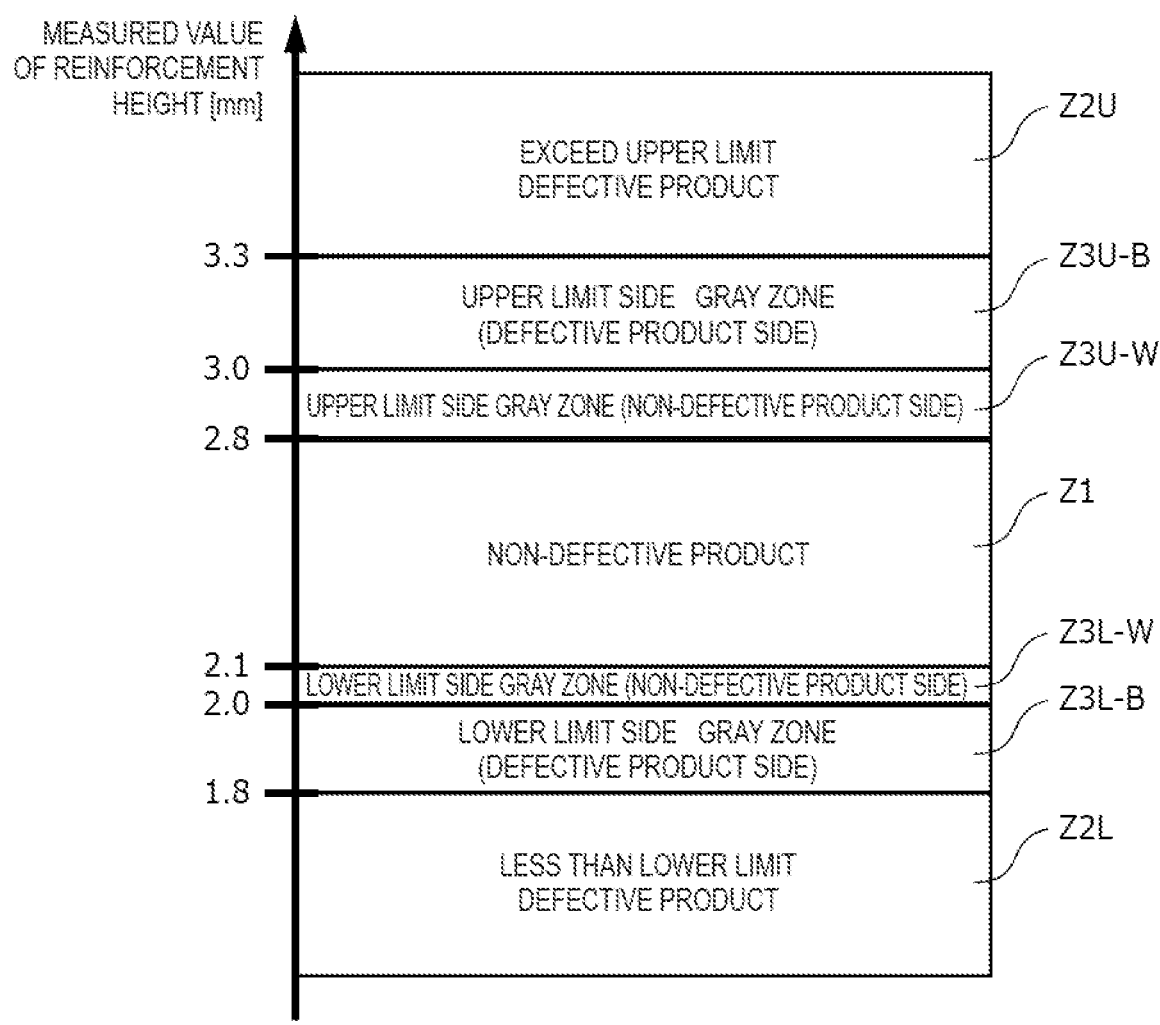
FIG. 10 is a conceptual diagram showing a second gray zone setting example of the bead appearance inspection.

FIG. 10 is a conceptual diagram showing a second gray zone setting example of the bead appearance inspection. A fact that the gray zone region is provided between the non-defective product zone Z1 determined to be a non-defective product and the defective product zone Z2U or Z2L determined to be a defective product is similar to that in the first gray zone setting example shown in FIG. 8. In the second gray zone setting example shown in FIG. 10, the gray zone is set to be divided into a plurality of stages. In this example, the gray zone is set to be divided into two stages including a non-defective product side gray zone and a defective product side gray zone. However, the gray zone may be set to be divided into three or more stages.

It is assumed that a reinforcement height of the non-defective workpiece is from 2.0 mm (lower limit threshold) to 3.0 mm (upper limit threshold). 2.0 mm and 3.0 mm are thresholds for non-defective product/defective product determination. The bead appearance inspection device (the host device 1, the inspection control device 3, or the like) can determine whether the welding result is non-defective/defective by comparing the value obtained from the input data (the point group data OD1) (for example, the measured value of the reinforcement height, the measured value indicating the diameter of the hole, the value of the standard deviation of the measured values, the score for determination, or the like) with the thresholds. For example, the bead appearance inspection device can determine that a workpiece is a non-defective product when the measured value of the reinforcement height is between 2.0 mm and 3.0 mm, and a workpiece is a defective product when the measured value of the reinforcement height is less than 2.0 mm or exceeds 3.0 mm. In the present example, two thresholds including the upper limit threshold of 3.0 mm and the lower limit threshold of 2.0 mm are set. However, only one threshold may be set, and it is possible to determine a non-defective product or a defective product based on whether the measured value, the score, or the like exceeds the thresholds.

In the example shown in FIG. 10, for the upper limit threshold, a non-defective product side gray zone Z3U-W having a reinforcement height from 2.8 mm to 3.0 mm and a defective product side gray zone Z3U-B having a reinforcement height from 3.0 mm to 3.3 mm are provided between the non-defective product zone Z1 having the reinforcement height of 2.8 mm or less and the defective product zone Z2U having the reinforcement height of more than 3.3 mm. Similarly, for the lower limit threshold, a non-defective product side gray zone Z3L-W having a reinforcement height from 2.0 mm to 2.1 mm and a defective product side gray zone Z3L-B having a reinforcement height from 1.8 mm to 2.0 mm are provided between the non-defective product zone Z1 having the reinforcement height of more than 2.1 mm and the defective product zone Z2L having the reinforcement height of less than 1.8 mm.

As in the example described above, the gray zone Z3U or Z3L is provided between the non-defective product zone Z1 determined to be a non-defective product and the defective product zone Z2U or Z2L determined to be a defective product. The gray zone Z3U is set to be divided into two stages including the non-defective product side gray zone Z3U-W and the defective product side gray zone Z3U-B. Similarly, the gray zone Z3L is also set to be divided into two stages including the non-defective product side gray zone Z3L-W and the defective product side gray zone Z3L-B. Here, a range of a value indicating the non-defective product side gray zone (for example, the reinforcement height of 2.8 mm to 3.0 mm) and a range of a value indicating the defective product side gray zone (for example, the reinforcement height of 3.0 mm to 3.3 mm) do not overlap each other.

As described above, since the gray zone is set to be divided into a plurality of stages, processing content for the workpiece after the appearance inspection can be made different in accordance with a stage of the gray zone. For example, it is possible to perform a more precise re-inspection of an appearance for a welding bead determined to be a non-defective product side gray, and to visually check a welding bead determined to be a defective product side gray by the user.

Figure 11:
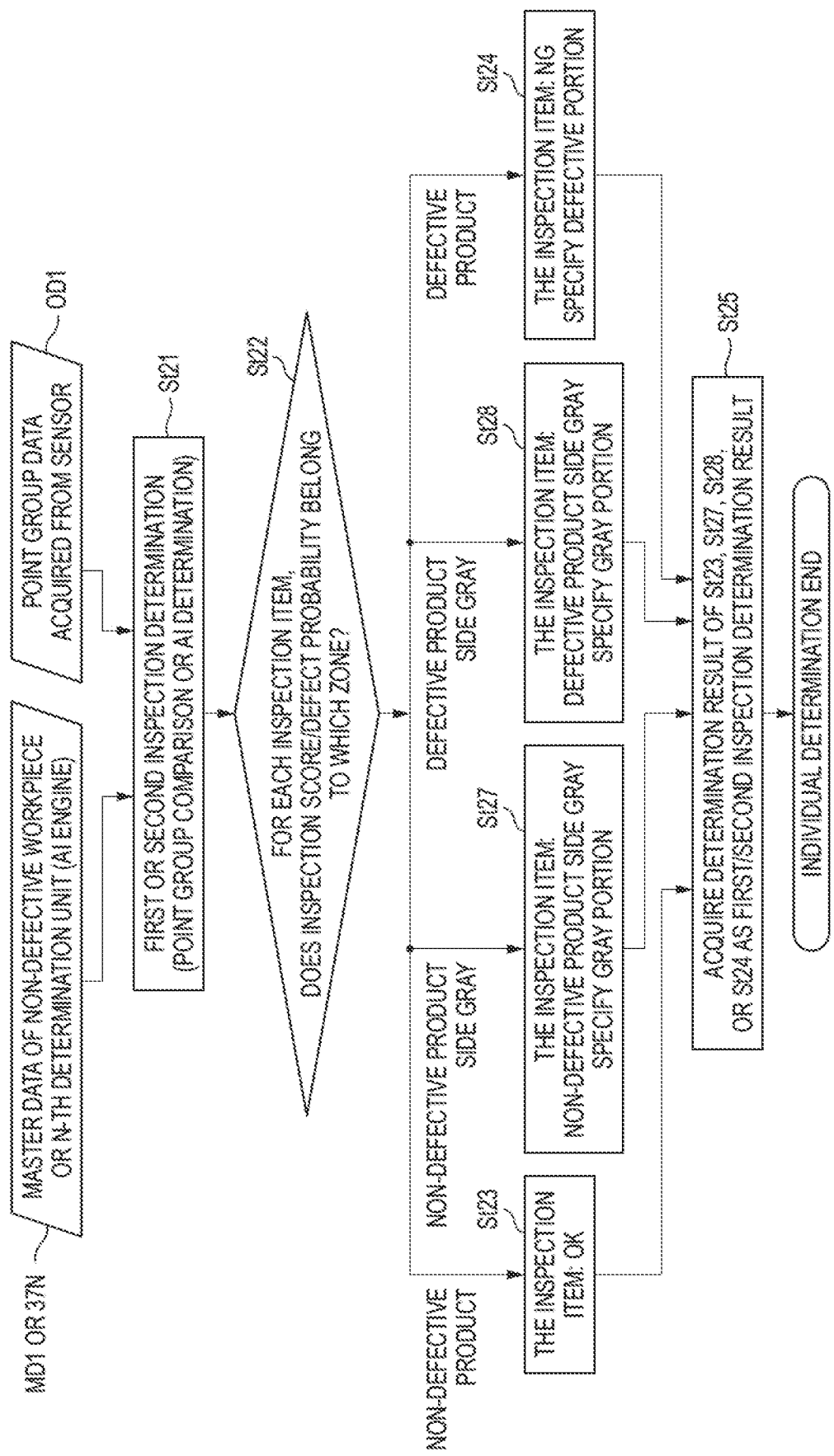
FIG. 11 is a flowchart showing an example of a processing procedure of an individual determination in the bead appearance inspection according to the second gray zone setting example of the bead appearance inspection.

FIG. 11 is a flowchart showing an example of a processing procedure of an individual determination in the bead appearance inspection according to the second gray zone setting example of the bead appearance inspection. The flowchart shown in FIG. 11 corresponds to both the first inspection determination (steps St21A to St25A) and the second inspection determination (steps St21B to St25B) shown in FIG. 4. The processing shown in FIG. 11 is similar when the processor 31 performs both the first inspection determination and the second inspection determination (see FIG. 3) and when the processor 31A performs the first inspection determination and the processor 11A performs the second inspection determination (see FIG. 7). Therefore, for convenience of description, the following description will be made assuming that a subject of the processing is a "processor".

The processor performs the first inspection determination (point group comparison) or the second inspection determination (AI determination) described above (St21). The processor determines, for each inspection item, which of the non-defective product zone (Z1), the non-defective product side gray zone (Z3U-W, Z3L-W), the defective product side gray zone (Z3U-B, Z3L-B), and the defective product zone (Z2U. Z2L) for the inspection item, the value of the inspection score (in the case of the first inspection determination) or the defect probability (in the case of the second inspection determination) belongs to (St22). The inspection score and the defect probability are values obtained from the input data (point group data OD1).

When determining that the value of the inspection score or the defect probability belongs to the non-defective product zone (Z1), the processor determines that the inspection item is "OK" (St23). When determining that the value of the inspection score or the defect probability belongs to the defective product zone (Z2U. Z2L), the processor determines that the inspection item is "NG" (St24). When determining that the value of the inspection score or the defect probability belongs to the non-defective product side gray zone (Z3U-W, Z3L-W), the processor determines that the inspection item is the "non-defective product side gray" (St27). When determining that the value of the inspection score or the defect probability belongs to the defective product side gray zone (Z3U-B. Z3L-B), the processor determines that the inspection item is the "defective product side gray" (St28). The processor acquires a determination result of step St23A, step St24, step St27, or step St28 as the first inspection determination result or the second inspection determination result (St25).

(Display of Bead Appearance Inspection Result)

Figure 12:
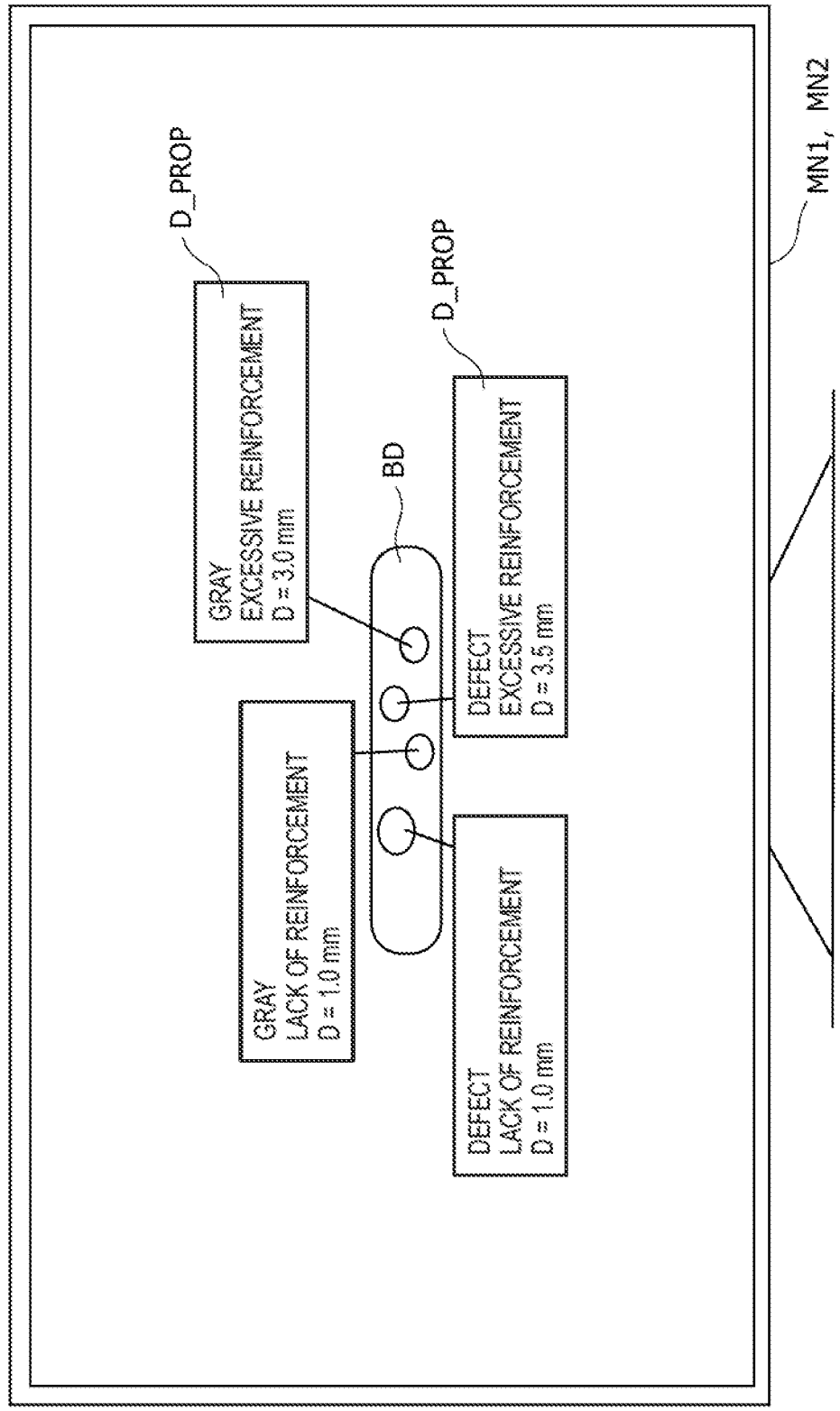

As described above, an appearance inspection result of a bead determined to be gray can be displayed to the user. FIG. 12 is a conceptual diagram showing a display example of a bead appearance inspection result by the monitors MN1 and MN2, and the like. A point group or an image indicating a bead BD after welding is displayed on a monitor or the like. A portion (defective portion or gray determination portion) determined to be defective or gray of the bead is displayed so as to be superimposed on the bead BD after welding. Display control on the monitor may be performed by, for example, the host device 1 or the inspection control device 3. Further, various pieces of property information D_PROP corresponding to portions determined to be defective or gray of the bead may be displayed. For example, as shown in FIG. 12, properties such as a determination result (defect, gray), a reason for being determined to be defective or gray (lack of reinforcement, excessive reinforcement, and the like), and a measured value (a reinforcement height in units of mm, or the like) based on an appearance result are displayed around the bead BD. As shown in the drawing, the property information D_PROP may be displayed in a balloon display mode.

A bead appearance inspection result may be displayed after welding (the main welding, and the repair welding when necessary) to a workpiece is finished. The bead appearance inspection result may be displayed before the repair welding is performed on the workpiece. Further, when the user performs a visual check (when the value of the inspection score or the defect probability belongs to the defective product side gray zone, and the like), the bead appearance inspection result may be displayed during an appearance inspection. The user can efficiently visually check a portion determined to be gray by checking the displayed bead appearance inspection result.

As described above, the gray determination can be performed in the appearance inspection for the workpiece in the boundary region between the non-defective product and the defective product. A more precise re-inspection or the visual check by the user can be performed for the welding bead determined to be gray. Therefore, the determination accuracy of the appearance inspection of the workpiece in the boundary region between the non-defective product and the defective product is improved. Further, the situations such as overlooking the defective product and erroneously detecting the non-defective product as the defective product can be avoided. Therefore, the productivity of the product on which welding is performed can be enhanced.

The range of the value indicating the gray zone is set based on the relative value for the upper limit value or lower limit value of the value obtained from the input data. Alternatively, the range of the value indicating the gray zone is set based on the absolute value of the value obtained from the input data. Accordingly, the gray zone can be flexibly set based on the value obtained from the input data.

The range of the value indicating the gray zone is divided into at least the range of the value indicating the first gray zone and the range of the value indicating the second gray zone, and the range of the value indicating the first gray zone and the range of the value indicating the second gray zone do not overlap each other. Accordingly, the gray zone can be set to be divided into the plurality of regions. For example, different processings can be performed for the workpiece having the welding bead determined to be gray such that a precise re-appearance inspection is performed for the welding bead belonging to the non-defective product side gray zone, the visual check by the user is performed for the welding bead belonging to the defective product side gray zone, and the like.

The welding bead, and on the welding bead, the gray determination portion where the value obtained from the input data is within the range of the value indicating the gray zone are displayed in a superimposed manner on the display device. Accordingly, the user can efficiently visually check the portion determined to be gray.

Although various embodiments are described above with reference to the drawings, it is needless to say that the present disclosure is not limited to such examples. It will be apparent to those skilled in the art that various alterations, modifications, substitutions, additions, deletions, and equivalents can be conceived within the scope of the claims, and it should be understood that such changes also belong to the technical scope of the present disclosure. Further, components in the various embodiments described above may be combined optionally within a range not departing from the spirit of the invention.

The present application is based on a Japanese Patent Application filed on Mar. 5, 2020 (Japanese Patent Application No. 2020-038205), and contents of which are incorporated herein by reference.

INDUSTRIAL APPLICABILITY

The present disclosure is useful as a bead appearance inspection device, a bead appearance inspection method, a program, and a bead appearance inspection system that more efficiently perform an appearance inspection of a welding bead of a workpiece produced by main welding.

REFERENCE SIGNS LIST 1, 1A: host device
2: robot control device
4: sensor
10, 20, 30: communication unit
11, 11A, 21, 31, 31A: processor
12, 22, 32: memory
13: cell control unit
23: main welding program creation unit
24: calculation unit
25: robot control unit
26: power supply control unit
33: inspection result storage unit
34: determination threshold storage unit
35: shape detection control unit
36: data processing unit
37: inspection result determination unit
371: first inspection determination unit
142: second inspection determination unit
14N, 37N: N-th inspection determination unit
100, 100A: welding system
200: manipulator
300: wire feeding device
301: welding wire
400: welding torch
500: power supply device
BD: bead
MC1: welding robot
MC1a: main welding robot
MC1b: repair welding robot
MN1, MN2: monitor
ST: external storage
Z1: non-defective product zone
Z2U, Z2L: defective product zone
Z3U, Z3L: gray zone
Z3U-W, Z3L-W: non-defective product side gray zone
Z3U-B, Z3L-B: defective product side gray zone

The invention claimed is:

1. A bead appearance inspection device comprising:
an input unit configured to enter input data related to a welding bead of a workpiece produced by welding; and
a determination unit configured to perform an inspection determination related to the welding bead based on the input data,
wherein the determination unit determines in which of a range of values of a non-defective product zone, a range of values of a gray zone, and a range of values of a defective product zone a value obtained from the input data is located,
wherein the non-defective product zone indicates the workpiece is not defective, the defective product zone indicates the workpiece is defective, and the gray zone indicates a final determination whether the workpiece is defective or not defective has not been made,
wherein the range of values of the gray zone is between the range of values of the non-defective product zone and the range of values of the defective product zone,
wherein the range of values of the gray zone is divided into at least a range of values of a first gray zone and a range of values of a second gray zone,
wherein the range of values of the first gray zone and the range of values of the second gray zone do not overlap each other,
wherein the first gray zone indicates a first additional inspection of the workpiece is to be performed to determine if the workpiece is defective or not defective, and the second gray zone indicates a second additional inspection of the workpiece is to be performed to determine if the workpiece is defective or not defective, and
wherein the first additional inspection and the second additional inspection are different inspections.

2. The bead appearance inspection device according to claim 1,
wherein the range of values of the gray zone is set based on a relative value for an upper limit value of the value obtained from the input data or a lower limit value of the value obtained from the input data.

3. The bead appearance inspection device according to claim 1,
wherein the range of values of the gray zone is set based on an absolute value of the value obtained from the input data.

4. The bead appearance inspection device according to claim 1,
wherein, when the value obtained from the input data is within the range of values of the gray zone, the welding bead, and on the welding bead a gray determination portion where the value obtained from the input data is within the range of values of the gray zone are displayed in a superimposed manner on a display device.

5. A bead appearance inspection method executed by a bead appearance inspection device, the bead appearance inspection method comprising:
an input step of inputting input data related to a welding bead of a workpiece produced by welding; and
a determination step of performing an inspection determination related to the welding bead based on the input data,
wherein, in the determination step, determining in which of a range of values of a non-defective product zone, a range of values of a gray zone, and a range of values of a defective product zone a value obtained from the input data to is located,
wherein the non-defective product zone indicates the workpiece is not defective, the defective product zone indicates the workpiece is defective, and the gray zone indicates a final determination whether the workpiece is defective or not defective has not been made,
wherein the range of values of the gray zone is between the range of values of the non-defective product zone and the range of values of the defective product zone,
wherein the range of values of the gray zone is divided into at least a range of values of a first gray zone and a range of values of a second gray zone,
wherein the range of values of the first gray zone and the range of values of the second gray zone do not overlap each other,
wherein the first gray zone indicates a first additional inspection of the workpiece is to be performed to determine if the workpiece is defective or not defective, and the second gray zone indicates a second additional inspection of the workpiece is to be performed to determine if the workpiece is defective or not defective, and
wherein the first additional inspection and the second additional inspection are different inspections.

6. A non-transitory computer readable storage medium having stored thereon a bead appearance inspection program that makes a computer perform the bead appearance inspection method according to claim 5.

7. A bead appearance inspection system comprising:
an input unit configured to enter input data related to a welding bead of a workpiece produced by welding; and
a determination unit configured to perform an inspection determination related to the welding bead based on the input data,
wherein the determination unit determines in which of a range of values of a non-defective product zone, a range of values of a gray zone, and a range of values of a defective product zone a value obtained from the input data is located,
wherein the non-defective product zone indicates the workpiece is not defective, the defective product zone indicates the workpiece is defective, and the gray zone indicates a final determination whether the workpiece is defective or not defective has not been made,
the range of values of the gray zone is between the range of values of the non-defective product zone and the range of values of the defective product zone,
wherein the range of values of the gray zone is divided into at least a range of values of a first gray zone and a range of values of a second gray zone,
wherein the range of values of the first gray zone and the range of values of the second gray zone do not overlap each other,
wherein the first gray zone indicates a first additional inspection of the workpiece is to be performed to determine if the workpiece is defective or not defective, and the second gray zone indicates a second additional inspection of the workpiece is to be performed to determine if the workpiece is defective or not defective, and
wherein the first additional inspection and the second additional inspection are different inspections.

* * * * *